United States Patent
Dodey et al.

(12) 
(10) Patent No.: US 6,384,222 B1
(45) Date of Patent: May 7, 2002

(54) N-BENZENESULFONYL-L-PROLINE COMPOUNDS, PREPARATION METHOD AND METHOD FOR USING THE COMPOUNDS IN THERAPY

(75) Inventors: Pierre Dodey; Michel Bondoux, both of Fontaine-les-Dijon; Patrick Houziaux, Bazemont; Martine Barth, Dijon; Khan Ou, Hauteville-les-Dijon, all of (FR)

(73) Assignee: Fournier Industrie et Sante, Paris (FR)

( * ) Notice: Subject to any disclaimer, the term of this patent is extended or adjusted under 35 U.S.C. 154(b) by 0 days.

(21) Appl. No.: 09/446,604
(22) PCT Filed: Jun. 11, 1998
(86) PCT No.: PCT/FR98/01211
§ 371 Date: Dec. 27, 1999
§ 102(e) Date: Dec. 27, 1999
(87) PCT Pub. No.: WO99/00387
PCT Pub. Date: Jan. 7, 1999

(30) Foreign Application Priority Data

Jun. 27, 1997 (FR) .............................. 97 08114

(51) Int. Cl.⁷ .................... C07D 471/04; C07D 473/12; A61K 31/517; A61K 31/495; A61P 11/06
(52) U.S. Cl. ...................... 544/282; 544/283; 544/353; 544/362; 546/121; 514/249; 514/253.04; 514/258; 514/259; 514/300
(58) Field of Search ................................ 544/282, 283, 544/353, 362; 546/121; 514/249, 253.04, 258, 259, 300

(56) References Cited

U.S. PATENT DOCUMENTS 4,217,130 A  8/1980  Tsuruta et al. .................. 71/95

FOREIGN PATENT DOCUMENTS

| EP | 0 622 361 A1 | 11/1994 |
| FR | 2 735 128 | 12/1996 |
| FR | 2 737 892 | 2/1997 |
| WO | WO 96/33171 | 10/1996 |
| WO | WO 97/25315 | 7/1997 |
| WO | WO 98/03503 | * 1/1998 |

* cited by examiner

*Primary Examiner*—Richard L. Raymond
*Assistant Examiner*—Venkataraman Balasubramanian
(74) *Attorney, Agent, or Firm*—Crowell & Moring LLP

(57) ABSTRACT

The present invention relates to compounds selected from the group consisting of:

(i) the compounds of the formula

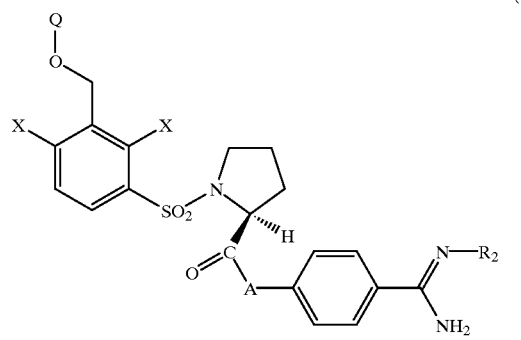

(I)

in which X is a halogen atom, A is a group $-NH-(CH_2)_n-NH-CO-$, $-NH-CH_2-$ or

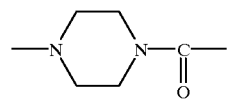

Q is a group

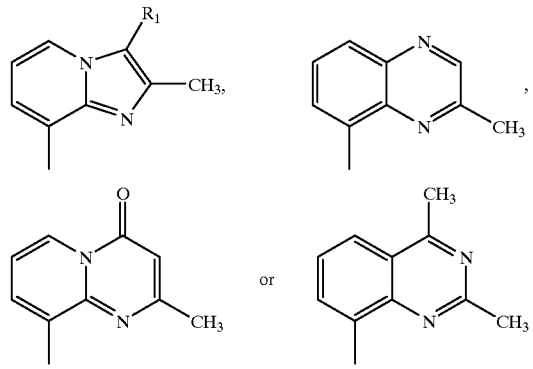

$R_1$ is hydrogen, halogen, $C_1-C_3$ alkyl or $C_1-C_5$ 1-oxoalkyl, $R_2$ is H or OH and n is 2, 3 or 4; and (ii) their addition salts.

It further relates to the process for their preparation and to their use in therapeutics, especially for combating pathological conditions involving bradykinin.

8 Claims, No Drawings

N-BENZENESULFONYL-L-PROLINE COMPOUNDS, PREPARATION METHOD AND METHOD FOR USING THE COMPOUNDS IN THERAPY

FIELD OF THE INVENTION

The present invention relates to novel compounds derived from N-(benzenesulfonyl)-(L)-proline, to the process for their preparation and to their use in therapeutics.

These novel compounds have an antagonistic action towards bradykinin and are useful in therapeutics, particularly for the treatment of pain and inflammation and especially for the treatment of asthma, cerebral traumatic shock and allergic rhinitis.

PRIOR ART

It is known that one of the possible treatments for certain pathological conditions of a painful and/or inflammatory nature (such as asthma, rhinitis, septic shock, toothache, etc.) is to inhibit the action of certain hormones such as bradykinin or kallidin. These peptide hormones are in fact involved in a large number of physiological processes, some of which are closely associated with these pathological conditions.

Although no product possessing this mode of action has yet been marketed, numerous studies have been undertaken in order to understand the mode of action of kinins, particularly bradykinin and its homologs, and then create compounds capable of antagonizing the bradykinin receptors. Pharmacological Reviews, vol. 44, no. 1, pages 1–80 (1992) and Biopolymers (Peptide Science), vol. 37, pages 143–155 (1995) may be mentioned among the numerous publications relating to this work.

Bradykinin is a peptide hormone consisting of 9 amino acids (Arg-Pro-Pro-Gly-Phe-Ser-Pro-Phe-Arg) and kallidin is a peptide hormone (Lys-Arg-Pro-Pro-Gly-Phe-Ser-Pro-Phe-Arg) which contains an additional amino acid (Lys) compared with bradykinin. It is known that earlier studies made it possible to obtain peptides which interact with the bradykinin receptors: some of them, like bradycor (CP.0127 from Cortech), icatibant (HOE 140 from Hoechst) ["bradycor" and "icatibant" are international non-proprietary names (INN)] or NPC 17761 (from Scios-Nova), have an inhibitory action on the binding of bradykinin to its $B_2$ receptor. Recent publications refer to other peptides capable of having an antagonistic action on bradykinin in respect of its $B_2$ receptor; examples of these publications which may be mentioned are WO-A-97/09347, WO-A-97/09346, U.S. Pat. No. 5,610,140, U.S. Pat. No. 5,620,958, U.S. Pat. No. 5,610,142 and U.S. Pat. No. 5,597,803. Furthermore, non-peptide compounds have been proposed as antagonists towards the binding of bradykinin to its $B_2$ receptor, especially in EP-A-0596406, EP-A-0622361, U.S. Pat. No. 5,578,601, FR-A-2735128, JP-A-09 040662, FR-A-2737892 and WO-A-97/11069. It is also known that certain compounds whose structure is more or less related to those of the compounds referred to in the present patent application have already been described for their possible anti-thrombotic properties, especially in the publications DE-A-3617183 and EP-A-0261539.

OBJECT OF THE INVENTION

There is a need for reducing or eliminating pain and inflammation in mammals and particularly in man.

To meet this need, a novel technical solution has been sought which is effective in the treatment of pain, irrespective of its origin, and especially in the treatment of pain associated with inflammatory phenomena or traumatisms.

According to the invention, it is proposed to provide a novel technical solution which involves competitive binding, at the bradykinin $B_2$ receptor, between (i) bradykinin and related or analogous hormones, and (ii) an antagonist, and utilizes compounds of the benzenesulfonamide type which are structurally different from the known products mentioned above and which are capable of limiting or substantially inhibiting the binding of bradykinin and analogous hormones to said bradykinin $B_2$ receptor.

According to this technical solution, the novel compounds bind competitively to the bradykinin $B_2$ receptor without causing the effects of bradykinin on this receptor (these novel compounds are said to be antagonists). This results in the appearance of a state analogous to that observed in the absence of bradykinin, namely a reduction in pain and in inflammatory reactions.

In accordance with this novel technical solution, it is proposed according to a first aspect of the invention to provide compounds derived from N-(benzenesulfonyl)-(L)-proline as novel industrial products, according to a second aspect of the invention to provide a process for the preparation of these compounds, and according to a third aspect of the invention to provide the use of these compounds, especially in therapeutics, as analgesics and/or anti-inflammatories.

SUBJECT OF THE INVENTION

In accordance with the novel technical solution of the invention, an N-(benzenesulfonyl)-L-proline compound is recommended as a novel industrial product, said compound being selected from the group consisting of:

(i) the compounds of formula I:

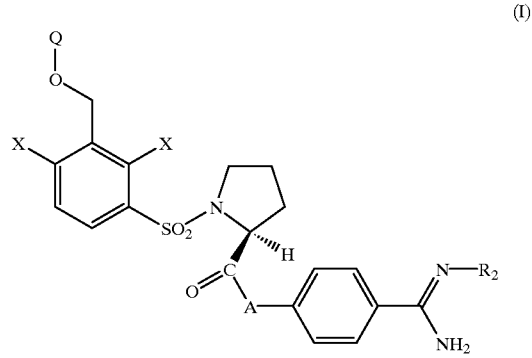

(I)

in which:

X is a halogen atom,

A is a divalent group

—NH—(CH$_2$)$_n$—NH—CO—, —NH—CH$_2$— or

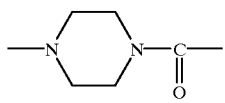

Q is a group

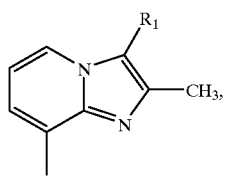

(Het 1)

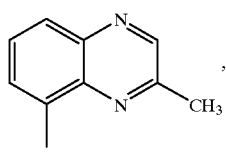

(Het 2)

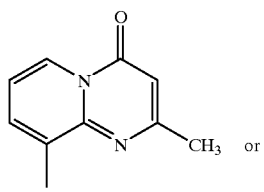

or (Het 3)

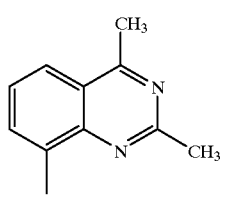

(Het 4)

$R_1$ is a hydrogen atom, a halogen atom, a $C_1$–$C_3$ alkyl group with a linear or branched hydrocarbon chain, or a $C_1$–$C_5$ 1-oxoalkyl group, $R_2$ is a hydrogen atom or an OH group, and n is 2, 3 or 4; and (ii) their addition salts.

According to the invention, a process for the preparation of the compounds of formula I and their addition salts is also recommended.

The use of a substance which antagonizes a receptor of bradykinin and analogous hormones is also recommended, wherein a bradykinin $B_2$ receptor antagonist selected from the compounds of formula I and their non-toxic addition salts is used for obtaining a drug intended for use in therapeutics to combat pathological conditions involving bradykinin or its analogs, in particular to combat pain, and especially in the treatment or prevention of pathological conditions associated with inflammatory or painful states.

DETAILED DESCRIPTION OF THE INVENTION

In general formula I of the compounds of the invention, halogen atom is understood as meaning a fluorine, chlorine, bromine or iodine atom, the preferred halogen being the chlorine atom.

$C_1$–$C_3$ alkyl group with a linear or branched hydrocarbon chain is understood here as meaning a methyl, ethyl, propyl or 1-methylethyl group.

$C_1$–$C_5$ 1-oxoalkyl group is understood as meaning acetyl, 1-oxopropyl, 1-oxobutyl and 2-methyl-1-oxopropyl groups.

In the compound of formula I, the nitrogen heterocycle of pyrrolidine structure comprises 1 asymmetric carbon atom. According to the invention, this carbon has the S configuration, which corresponds to the configuration of L-proline.

"Addition salts" are understood as meaning the acid addition salts obtained by reacting a compound of formula I with a mineral acid or an organic acid. The preferred mineral acids for salifying a basic compound of formula I are hydrochloric, hydrobromic, phosphoric and sulfuric acids. The preferred organic acids for salifying a basic compound of formula I are methanesulfonic, benzenesulfonic, maleic, fumaric, oxalic, citric, lactic and trifluoroacetic acids.

"Room temperature" is understood here as meaning a temperature of 15 to 25° C. and "temperature close to room temperature" is understood here as meaning a temperature of 0 to 40° C. and preferably of 10 to 35° C.

The general process recommended according to the invention for the preparation of the compounds of formula I comprises, according to a first variant A, the steps which consist in:

(1) reacting a hydroxylated heterocyclic compound of the formula

Q-O-Met in which:

Met is an alkali metal, especially Na or K, and

Q is a heterocyclic group selected from the structures Het 1, Het 2, Het 3 and Het 4:

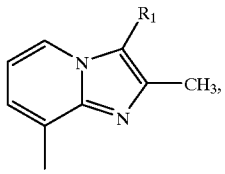

(Het 1)

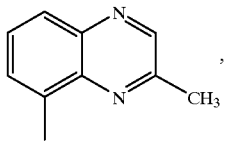

(Het 2)

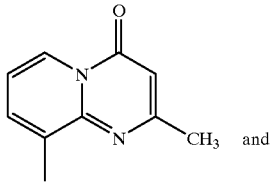

and (Het 3)

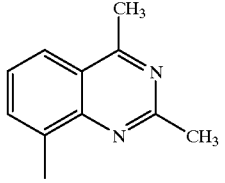

(Het 4)

$R_1$ being a hydrogen atom or a $C_1$–$C_3$ alkyl group, with a compound of formula II:

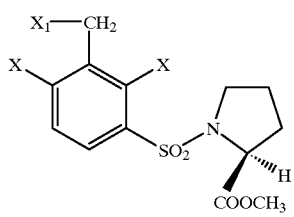

(II)

in which X is a halogen atom and $X_1$ is a halogen atom, preferably a bromine atom, in an anhydrous solvent, for example dimethylformamide, at a temperature of between 0 and 50° C., for 0.5 to 10 hours, to give a compound of formula III:

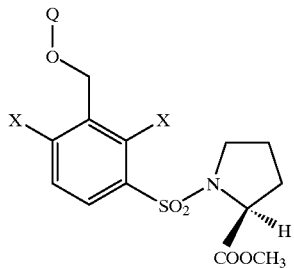

(III)

in which Q, X and $R_1$ are as defined above;

(2) if necessary, if Q in the compound of formula III is the group Het 1 in which $R_1$ is a hydrogen atom:

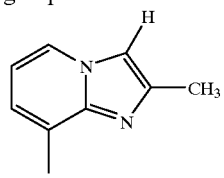

reacting said compound of formula III with a halogenating agent such as N-bromosuccinimide or N-chlorosuccinimide, in an appropriate solvent, especially a halogenated solvent, an ether or an alcohol, at a temperature of between about 0 and 50° C., for 0.5 to 20 hours, to give a compound of formula III':

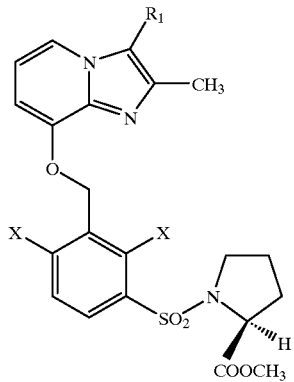

(III')

in which:
$R_1$ is a halogen atom, preferably bromine or chlorine;

(3) hydrolyzing the ester group of the compound of formula III or III' obtained according to one of steps (1) or (2) above, especially by reaction with aqueous sodium hydroxide solution in a miscible solvent such as methanol, at a temperature of the order of 20 to 60° C., for 1 to 5 hours, to give, after acidification, a compound of formula IV:

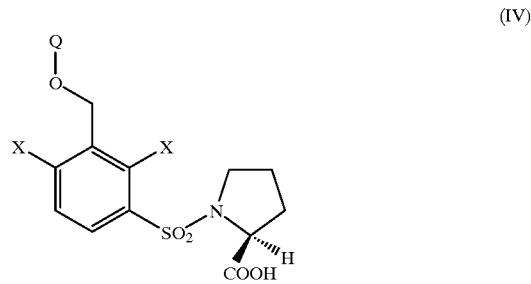

(IV)

in which Q and X are as defined above and $R_1$ is a hydrogen atom, a halogen atom or a $C_1$–$C_3$ alkyl group;

(4) reacting the resulting compound of formula IV with the salt of an amine of the formula

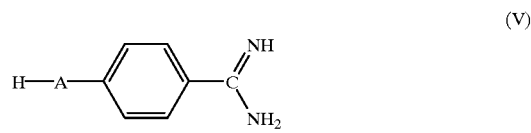

(V)

in which A is a group $$-NH-(CH_2)_n-NH-CO-, -NH-CH_2- \text{ or}$$

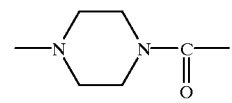

in which n is 2, 3 or 4, in an appropriate solvent, especially dichloromethane, in the presence of activators such as, in particular, 1-hydroxy-7-azabenzotriazole (HOAT) and 1-[3-(dimethylaminopropyl)-3-ethyl]carbodiimide (EDCI) hydrochloride, at a temperature close to room temperature (10–35° C.), for 2 to 50 hours, to give a compound of formula I in which $R_2$ is H:

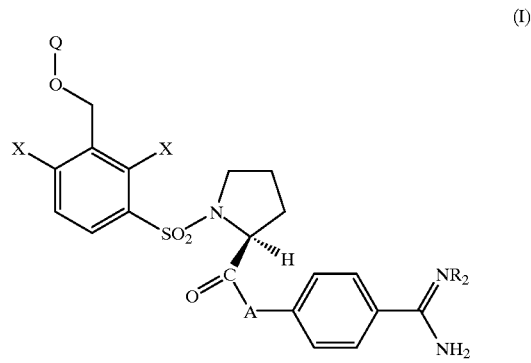

(I)

in which A, Q, X and $R_1$ are as defined above and $R_2$, is H; and (5) if necessary, reacting the resulting compound of formula I with an acid to give the corresponding acid addition salt;

according to a second variant B, the steps which consist in:
(1) reacting the acid compound of formula IV, obtained for example in step (3) of variant A, in which $R_1$ is a hydrogen atom, a chlorine atom, a $C_1$–$C_3$ alkyl group with a linear or branched hydrocarbon chain, or a $C_1$–$C_5$ 1-oxoalkyl group, with a compound of formula VI:

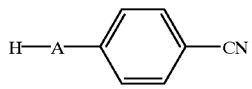
(VI)

in which A is a group

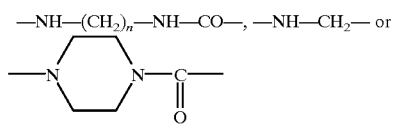

in which n is 2, 3 or 4,
under conditions analogous to those recommended for carrying out step (4) of variant A above, to give a compound of formula VII:

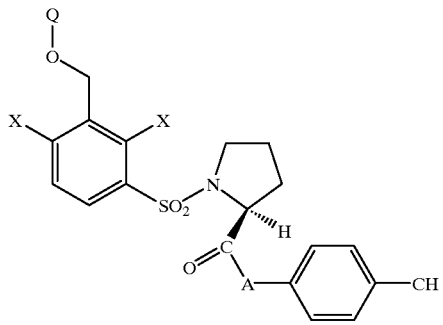
(VII)

in which Q, $R_1$, X and A are as defined in the starting, materials;

(2) reacting the resulting compound of formula VII with hydroxylamine (freed from its hydrochloride by the action, in the reaction medium, of an aprotic strong base such as triethylamine) in an appropriate solvent, especially an aprotic solvent such as dimethyl sulfoxide (DMSO), at room temperature (15–25° C.), for 1 to 12 hours, to give a compound of formula VIII:

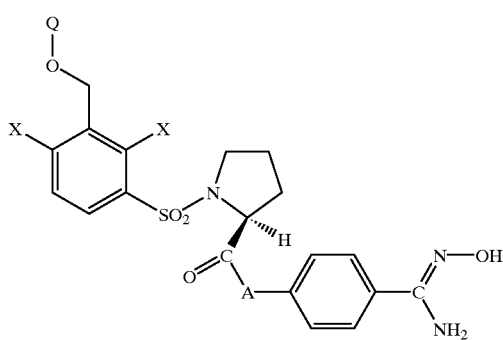
(VIII)

in which Q, $R_1$, X and A are as defined above;
(3) acetylating the resulting compound of formula VIII, at a temperature close to room temperature, for 1 to 8 hours, to give the compound of formula IX:

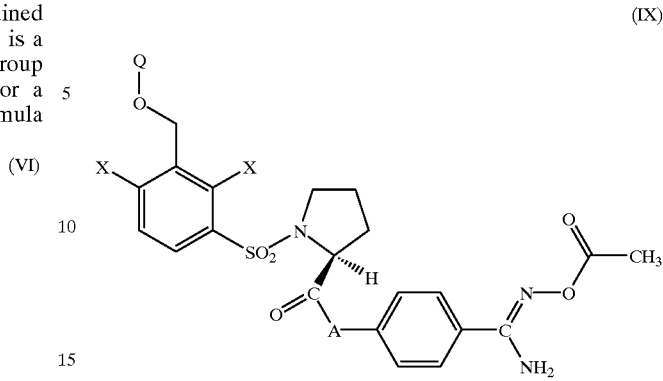
(IX)

in which Q, $R_1$, X and A are as defined above; and
(4) reducing the resulting compound of formula IX by catalytic hydrogenation, especially in a solvent such as methanol, in the presence of a hydrogenation catalyst such as Lindlar's catalyst, at a temperature close to room temperature, under a hydrogen pressure of between $10^5$ and $10^6$ Pascals, to give the compound of formula I in which Q, $R_1$, X and A are as defined above and $R_2$ is H;

according to a third variant C, the steps which consist in:

(1) reacting the compound of formula IV, obtained according to step (3) of variant A, with an amine of the formula

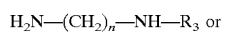

in which n is 2, 3 or 4, and
$R_3$ is an amino-protecting group such as the "Boc" (1,1-dimethylethoxycarbonyl) group,
under operating conditions analogous to those recommended for carrying out step (4) of variant A, to give a compound of formula X:

(X)

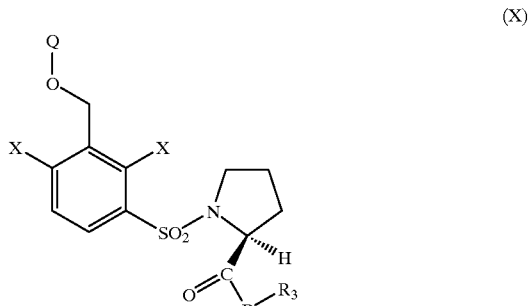

in which B is

—NH—(CH$_2$)$_n$—NH— or

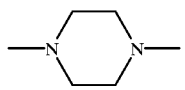

and Q, R$_1$ and X are as defined above;

(2) deprotecting the amine group of the resulting compound of formula X so as to replace the group R$_2$ with a hydrogen atom, for example, if R$_3$ is the Boc group, by reaction with an acid in solution in a solvent such as ethyl acetate, at room temperature, for 4 to 30 hours, to give the compound of formula XI:

(XI)

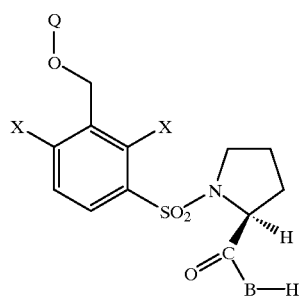

in which B, Q, R$_1$ and X are as defined above; and (3) reacting the resulting compound of formula XI with 4-(aminoiminomethyl)-benzoic acid, under conditions analogous to those previously described in step (4) of variant A above, to give the compound of formula I in which R$_2$ is H:

(I)

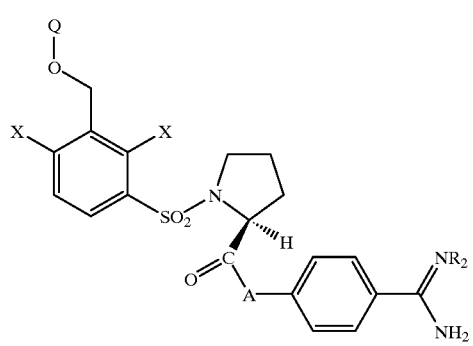

in which:

Q, R$_1$ and X are as defined above, R$_2$ is H and A is a group

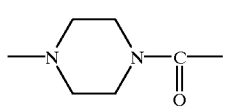

and according to a fourth variant D, the steps which consist in:

(1) reacting the acid of the formula (XII)

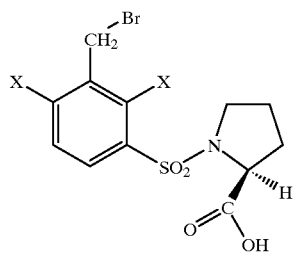

in which X is a halogen,
with a compound of the formula

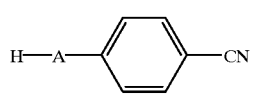

in which A is a group

—NH—(CH$_2$)$_n$—NH—CO—, —NH—CH$_2$— or

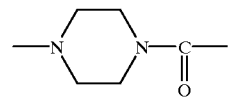

in which n is 2, 3 or 4, under reaction conditions analogous to those recommended for carrying out step (4) of variant A above, to give the compound of formula XIII:

(XIII)

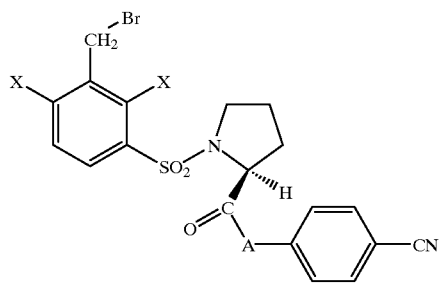

in which A and X are as defined above;

(2) reacting the resulting compound of formula XIII with a hydroxylated heterocyclic derivative of the general structure Q-OH, Q being selected from the structures (Het 1)

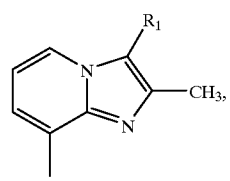

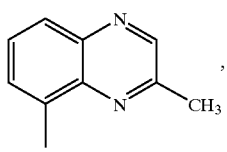
(Het 2)

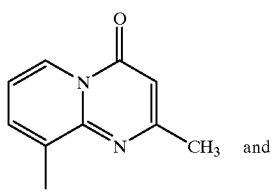
(Het 3) and

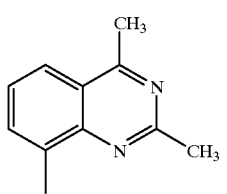
(Het 4)

in which $R_1$ is a hydrogen atom, a halogen atom, a $C_1$–$C_3$ alkyl group or a $C_1$–$C_5$ 1-oxoalkyl group,
under operating conditions analogous to those described for carrying out step (1) of variant A above, to give the compound of formula XIV:

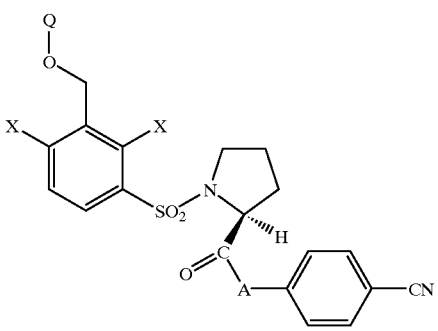
(XIV)

in which Q, $R_1$, X and A are as defined in the starting materials; and (3) then performing, on the resulting compound of formula XIV, a series of reactions analogous to those previously described in steps (2), (3) and (4) of variant B above, to give the compound of formula I according to the invention in which Q, X, $R_1$ and A are as defined in the starting compounds.

The invention will be understood more clearly from the following description of (i) Preparatory Examples and (ii) results of pharmacological tests performed with compounds according to the invention. Of course, these details as a whole do not imply a limitation but are given by way of illustration.

In the case of compounds which have an asymmetric carbon in their structure, the absence of a particular indication, or the notation (R,S), means that the compounds are racemic; in the case of compounds which exhibit chirality, this is indicated immediately after the numbering of the substituent carried by said asymmetric carbon; the symbol (R) or (S) is then used in accordance with the Cahn-Ingold-Prelog rules. The nomenclature used in the Examples is that recommended by Chemical Abstracts; thus, after reaction of the acid group with an amine, certain L-proline derivatives may become 2(S)-pyrrolidinecarboxamide derivatives.

In the experimental section, the "Preparations" relate to the intermediates and the "Examples" relate the products according to the invention.

The melting points (m.p.) indicated below are generally measured using a Kofler bench and are not corrected, so they represent instantaneous melting points.

The spectral characteristics of the nuclear magnetic resonance (NMR) signals are given for the proton ($^1$H) or for the 13 isotope of carbon ($^{13}$C); the chemical shift is indicated relative to the tetramethylsilane signal and is followed, in brackets, by the shape of the signal (s for singlet, d for doublet, t for triplet, q for quadruplet, m for multiplet, bs for broad signal) and the number of protons corresponding to the signal. By way of indication, the $^1$H NMR spectra were run at 300 MHz.

PREPARATION I

N-[[3-[[2-Methylimidazo[1,2-a]pyridin-8-yl]oxymethyl]-2,4-dichlorophenyl]-sulfonyl]-L-proline Methyl Ester A solution of 10 g (67.10$^{-3}$ mol) of 2-methyl-8-hydroxyimidazo[1,2-a]-pyridine in 300 ml of dimethylformamide (DMF) is prepared and 2.02 g (67.10$^{-3}$ mol) of an 80% suspension of sodium hydride in oil are added. The mixture is stirred at room temperature for 30 min and a solution of 2.91 g (67.10$^{-3}$ mol) of N-[[3-(bromomethyl)-2,4-dichlorophenyl]sulfonyl]-L-proline methyl ester in 100 ml of DMF is then added. After stirring at room temperature for 15 hours, the reaction mixture is poured into 500 ml of water and extracted 3 times with ethyl acetate. The combined organic phases are washed with water, dried over sodium sulfate and concentrated under reduced pressure. The resulting crude product is purified by chromatography on silica gel (silica gel 60 of particle size 15 to 40 μm) using a toluene/2-propanol mixture (96/4; v/v) as the eluent to give 22.5 g of the expected product in the form of a pinkish solid (yield=67%).

M.p.=149° C.; $[\alpha]_D^{23}$=19.0° (c=1.5; CHCl$_3$).

PREPARATION II

N-[[3-[[2-Methylimidazo[1,2-a]pyridin-8-yl]oxymethyl]-2,4-dichlorophenyl]-sulfonyl]-L-proline A solution of 12.2 g (24.10$^{-3}$ mol) of the compound obtained according to Preparation I in 180 ml of methanol and 120 ml of water is prepared and 48 ml of 1 N sodium hydroxide solution are then added. The reaction mixture is heated to 40° C. and stirred for 1.5 hours. The methanol is evaporated off under reduced pressure, the residue is cooled, 200 ml of water are added and the mixture is acidified to pH 2 by the slow addition of 1 N hydrochloric acid solution, with stirring. The medium is extracted with dichloromethane and the organic phase obtained is dried over sodium sulfate and concentrated under reduced pressure to give 11.6 g of the expected product in the form of pinkish white crystals.

M.p.=135° C.; $[\alpha]_D^{22}$=−50.7° (c=1.02; CH$_2$Cl$_2$).

PREPARATION III

[3-[(4-Cyanobenzoyl)amino]propyl]carbamic acid 1,1-dimethylethyl Ester

A solution of 10 g (57.10$^{-3}$ mol) of (3-aminopropyl)carbamic acid 1,1-dimethylethyl ester (or N-Boc-1,3- propanediamine) in 75 ml of dichloromethane is prepared and 15.9 ml ($114.10^{-3}$ mol) of triethylamine are added. The mixture is cooled with an ice bath and 10.38 g ($60.10^{-3}$ mol) of 4-cyanobenzoyl chloride are added gradually. The reaction medium is allowed to warm up to room temperature, stirred for 10 hours and then poured into 150 ml of water. It is extracted with dichloromethane and the organic phase obtained is washed with 1 N hydrochloric acid solution and then with water and is finally dried over sodium sulfate and concentrated under reduced pressure to give 16.4 g of the expected product in the form of ochre crystals (yield=94%).

$^1$H NMR (DMSO): 1.37 (s, 9H); 1.63 (m, 2H); 2.97 (m, 2H); 3.26 (m, 2H); 6.84 (t, 1H); 7.97 (s, 4H); 8.70 (t, 1H).

PREPARATION IV

N-(3-Aminopropyl)-4-cyanobenzamide Hydrochloride 16.4 g ($54.10^{-3}$ mol) of the compound obtained according to Preparation III are dissolved in 150 ml of ethyl acetate, and 104 ml of a solution of hydrogen chloride containing 2.6 mol/l in ethyl acetate are then added. The mixture is stirred at room temperature for 24 hours and then concentrated under reduced pressure. The resulting crude product is washed with ethyl ether and dried under vacuum at 40° C. to give 12.15 g of the expected product in the form of an off-white solid (yield=94%).

M.p.=176–180° C.

PREPARATION V

1-[[3-[[2-Methylimidazo[1,2-a]pyridin-8-yl]oxymethyl]-2,4-dichlorophenyl]-sulfonyl]-N-[3-[(4-cyanobenzoyl)amino]propyl]-2(S)-pyrrolidinecarboxamide A solution of 5.8 g ($12.10^{-3}$ mol) of the compound obtained according to Preparation II in 200 ml of dichloromethane is prepared and 2.53 g ($13.10^{-3}$ mol) of EDCI [1-(3-dimethylaminopropyl)-3-ethylcarbodiimide] and 1.79 g ($13.10^{-3}$ mol) of HOAT (1-hydroxy-7-azabenzotriazole) are then added. The resulting mixture is stirred for 30 min at room temperature and a solution of 2.69 g ($12.10^{-3}$ mol) of the compound obtained according to Preparation IV in a mixture of 150 ml of dichloromethane and 2.6 ml ($24.10^{-3}$ mol) of N-methylmorpholine is then added. The reaction medium is stirred for 16 hours at room temperature and then washed successively with water, with 0.5 N hydrochloric acid solution, with sodium bicarbonate solution and finally with water again. After drying over sodium sulfate, the organic phase is concentrated under reduced pressure and the crude product obtained is purified by chromatography on silica gel using a dichloromethane/methanol mixture (97/3; v/v) as the eluent to give 6.66 g of the expected product in the form of white crystals (yield=83%).

M.p.=100–102° C.; $[\alpha]_D^{23}$=-15° (c=0.99; $CH_2Cl_2$).

EXAMPLE 1

1-[[3-[[2-Methylimidazo[1,2-a]pyridin-8-yl]oxymethyl]-2,4-dichlorophenyl]-sulfonyl]-N-[3-[[4-[(amino)(hydroxyimino)methyl]benzoyl]amino]propyl]-2(S)-pyrrolidinecarboxamide A solution of 6.53 g ($9.7.10^{-3}$ mol) of the compound obtained according to Preparation V in 100 ml of dimethyl sulfoxide (DMSO) is prepared and 1.36 g ($19.10^{-3}$ mol) of hydroxylamine hydrochloride and then 2.7 ml ($19.10^{-3}$ mol) of triethylamine are added. The reaction mixture is stirred for 3 hours at room temperature, the same amounts of hydroxylamine hydrochloride and triethylamine are then added again and the reaction medium is stirred for 8 hours. It is poured into 400 ml of water, with stirring, and the precipitate obtained is filtered off and redissolved in dichloromethane. The organic phase obtained is washed with water and then dried over sodium sulfate. After removal of the solvent under reduced pressure, 5.37 g of the expected product are obtained in the form of white crystals (yield= 78%).

M.p.=135° C.; $[\alpha]_D^{22}$=-6.9° (c=1.04; DMSO).

PREPARATION VI

1-[[3-[[2-Methylimidazo[1,2-a]pyridin-8-yl]oxymethyl]-2,4-dichlorophenyl]-sulfonyl]-N-[3-[[4-[(acetoxyimino)(amino)methyl]benzoyl]amino]propyl]-2(S)-pyrrolidinecarboxamide A solution of 5.28 g ($7.5.10^{-3}$ mol) of the compound obtained according to Example 1 in 150 ml of dichloromethane is prepared and 0.96 ml ($10.10^{-3}$ mol) of acetic anhydride is added. After stirring at room temperature for 15 hours, the reaction medium is concentrated under reduced pressure to give 5.48 g of the expected product in the form of beige crystals.

M.p.=105–107° C.; $[\alpha]_D^{20}$=-19° (c=1.0; $CH_3OH$).

EXAMPLE 2

1-[[3-[[2-Methylimidazo[1,2-a]pyridin-8-yl]oxymethyl]-2,4-dichlorophenyl]-sulfonyl]-N-[3-[[4-(aminoiminomethyl)benzoyl]amino]propyl]-2(S)-pyrrolidinecarboxamide A solution of 5.4 g ($7.2.10^{-3}$ mol) of the compound obtained according to Preparation VI in 150 ml of methanol is prepared and 1.08 g of Lindlar's catalyst (containing 5% of palladium) are added. The mixture is stirred under a hydrogen atmosphere, under a pressure of $3.10^5$ Pascals, for 5 hours, at room temperature. After the catalyst has been filtered off, the solvent is removed by evaporation under reduced pressure and the crude product is purified by chromatography on $NH_2$ grafted silica gel ("Lichroprep $NH_2$") using a dichloromethane/methanol mixture (95/5; v/v) as the eluent to give 2.02 g of the expected product in the form of white crystals (yield=41%).

M.p.=120–125° C.; $[\alpha]_D^{25}$=-36° (c=1.03; $CH_3OH$).

EXAMPLE 3

1-[[3-[[2-Methylimidazo[1,2-a]pyridin-8-yl]oxymethyl]-2,4-dichlorophenyl]-sulfonyl]-N-[3-[[4-(aminoimiomethyl)benzoyl]amino]propyl]-2(S)-pyrrolidinecarboxamide Methanesulfonate A solution of 1.95 g ($2.8.10^{-3}$ mol) of the compound obtained according to Example 2 in 14 ml of methanol is prepared. 184 μl ($2.8.10^{-3}$ mol) of methanesulfonic acid are added, with stirring. After stirring for 30 min at room temperature, the reaction medium is poured into 500 ml of ethyl ether. The precipitate obtained is filtered off, washed with ether and dissolved in 60 ml of distilled water. The solution obtained is lyophilized to give 2.07 g of the expected product in the form of white crystals (yield 94%).

M.p.=170–172° C.; $[\alpha]_D^{25}$=-38.2° (c=1.03;$CH_3OH$).

PREPARATION VII 4-(4-Cyanobenzoyl)-1-piperazinecarboxylic Acid 1, 1-Dimethylethyl Ester The expected product is obtained in the form of white crystals (yield=90%) by following a procedure analogous to Preparation III, starting from 1-piperazinecarboxylic acid 1,1-dimethylethyl ester.

$^1$H NMR: 1.46 (s, 9H); 3.38 (m, 4H); 3.51 (m, 2H); 3.73 (m, 2H); 7.50 (d, 2H) 7.73 (d, 2H).

PREPARATION VIII 1-(4-Cyanobenzoyl)piperazine Hydrochloride

The expected product is obtained in the form of white crystals (yield=99%) by following a procedure analogous to Preparation IV, starting from the compound obtained according to Preparation VII.

M.p.=262–264° C.

PREPARATION IX

1-[[3-[[2-Methylimidazo[1,2-a]pyridin-8-yl] oxymethyl]-2,4-dichlorophenyl]-sulfonyl]-2(S)-[[4-(4-cyanobenzoyl)piperazin-1-yl]carbonyl]pyrrolidine The expected product is obtained in the form of white crystals (yield=93%) by following a procedure analogous to Preparation V, starting from the compound obtained according to Preparation VIII.

M.p.=112–115° C.; $[\alpha]_D^{21}$=+2.8° (c=1.03; $CH_2Cl_2$).

EXAMPLE 4

1-[[3-[[2-Methylimidazo[1,2-a]pyridin-8-yl] oxymethyl]-2,4-dichlorophenyl]-sulfonyl]-2(S)-[[4-[4-[(amino)(hydroxyimino)methyl]benzoyl] piperazin-1-yl]carbonyl]pyrrolidine The expected product is obtained in the form of white crystals (yield=84%) by following a procedure analogous to Example 1, starting from the compound obtained according to Preparation IX.

M.p.=165–167° C.; $[\alpha]_D^{23}$=+9.60 (c=1.04; DMSO).

PREPARATION X

1-[[3-[[2-Methylimidazo[1,2-a]pyridin-8-yl] oxymethyl]-2,4-dichlorophenyl]sulfonyl]-2(S)-[[4-[4-[(acetoxyimino)(amino)methyl]benzoyl] piperazin-1-yl]carbonyl]pyrrolidine The expected product is obtained in the form of white crystals (yield=98%) by following a procedure analogous to Preparation VI, starting from the compound obtained according to Example 4.

M.p.=115–118° C.; $[\alpha]_D^{23}$=+10.2° (c=1; DMSO).

EXAMPLE 5

1-[[3-[[2-Methylimidazo[1,2-a]pyridin-8-yl] oxymethyl]-2,4-dichlorophenyl]sulfonyl]-2(S)-[[4-[4-(aminoiminomethyl)benzoyl]piperazin-1-yl] carbonyl]pyrrolidine The expected product is obtained in the form of pale yellow crystals (yield=60%) by following a procedure analogous to Example 2, starting from the compound obtained according to Preparation X.

M.p.=159–161° C.; $[\alpha]_D^{24}$=−30° (c=1.02; $CH_3OH$).

EXAMPLE 6

1-[[3-[[2-Methylimidazo[1,2-a]pyridin-8-yl] oxymethyl]-2,4-dichlorophenyl]sulfonyl]-2(S)-[[4-[4-(aminoiminomethyl)benzoyl]piperazin-1-yl] carbonyl]pyrrolidine Methanesulfonate The expected product is obtained in the form of white crystals (yield=93%) by following a procedure analogous to Example 3, starting from the compound obtained according to Example 5.

M.p.=172–174° C.; $[\alpha]_D^{26}$=−19.3° (c=1.01; $CH_3OH$).

PREPARATION XI

N-[[3-[[2,3-Dimethylimidazo[1,2-a]pyridin-8-yl] oxymethyl]-2,4-dichlorophenyl]sulfonyl]-L-proline Methyl Ester The expected product is obtained in the form of beige crystals (yield=50%) by following a procedure analogous to Preparation I, starting from 2,3-dimethyl-8-hydroxyimidazo [1,2-a]pyridine.

M.p.=128–130° C.; $[\alpha]_D^{29}$=−8.4° (c=0.97; $C_2H_5OH$).

PREPARATION XII

N-[[3-[[2,3-Dimethylimidazo[1,2-a]pyridin-8-yl] oxymethyl]-2,4-dichlorophenyl]sulfonyl]-L-proline The expected product is obtained in the form of off-white crystals (yield=60%) by following a procedure analogous to Preparation II, starting from the compound obtained according to Preparation XI.

M.p.=140–145° C.; $[\alpha]_D^{22}$=+15.8° (c=0.99; $C_2H_5OH$).

PREPARATION XIII

1-[[3-[[2,3-Dimethylimidazo[1,2-a]pyridin-8-yl] oxymethyl]-2,4-dichlorophenyl]sulfonyl]-N-[3-[(4-cyanobenzoyl)amino]propyl]-2(S)-pyrrolidinecarboxamide The expected product is obtained in the form of beige crystals (yield=62%) by following a procedure analogous to Preparation V, starting from the compound obtained according to Preparation XII.

M.p.=128–130° C.; $[\alpha]_D^{26}$=−7° (c=0.95; $CH_2Cl_2$).

EXAMPLE 7

1-[[3-[[2,3-Dimethylimidazo[1,2-a]pyridin-8-yl] oxymethyl]-2,4-dichlorophenyl]sulfonyl]-N-[3-[[4-[(amino)(hydroxyimino)methyl]benzoyl]amino] propyl]-2(S)-pyrrolidinecarboxamide The expected product is obtained in the form of off-white crystals (yield=74%) by following a procedure analogous to Example 1, starting from the compound obtained according to Preparation XIII.

M.p.=131–133° C.; $[\alpha]_D^{24}$=−9.5° (c=1.01; DMSO).

PREPARATION XIV

1-[[3-[[2,3-Dimethylimidazo[1,2-a]pyridin-8-yl] oxymethyl]-2,4-dichlorophenyl]sulfonyl]-N-[3-[[4-[(acetoxyimino)(amino)methyl]benzoyl]amino] propyl]-2(S)-pyrrolidinecarboxamide The expected product is obtained in the form of white crystals (yield=98%) by following a procedure analogous to Preparation VI, starting from the compound obtained according to Example 7.

M.p.=140–142° C.; $[\alpha]_D^{22}$=−7.5° (c=1.00; DMSO).

EXAMPLE 8

1-[[3-[[2,3-Dimethylimidazo[1,2-a]pyridin-8-yl] oxymethyl]-2,4-dichlorophenyl]sulfonyl]-N-[3-[[4-(iminoaminomethyl)benzoyl]amino]propyl]-2(S)-pyrrolidinecarboxamide The expected product is obtained in the form of pale yellow crystals (yield=53%) by following a procedure analogous to Example 2, starting from the compound obtained according to Preparation XIV.

M.p.=150–152° C.; $[\alpha]_D^{25}$=−15.5° (c=1.1; $CH_2Cl_2$).

EXAMPLE 9

1-[[3-[[2,3-Dimethylimidazo[1,2-a]pyridin-8-yl] oxymethyl]-2,4-dichlorophenyl]sulfonyl]-N-[3-[[4-(aminoiminomethyl)benzoyl]amino]propyl]-2(S)-pyrrolidinecarboxamide Methanesulfonate The expected product is obtained in the form of white crystals (yield=82%) by following a procedure analogous to Example 3, starting from the compound obtained according to Example 8.

M.p.=179–181° C.; $[\alpha]_D^{23}$=−39° (c=1.02; $CH_3OH$).

PREPARATION XV

1-[[3-[[2,3-Dimethylimidazo[1,2-a]pyridin-8-yl] oxymethyl]-2,4-dichlorophenyl]sulfonyl]-2(S)-[[4-(4-cyanobenzoyl)piperazin-1-yl]carbonyl]pyrrolidine The expected product is obtained in the form of yellow crystals (yield=41%) by following a procedure analogous to Preparation IX, starting from the compound obtained according to Preparation XII.

M.p.=125–128° C.; $[\alpha]_D^{26}$=+0.9° (c=0.85; $CH_2Cl_2$).

EXAMPLE 10

1-[[3-[[2,3-Dimethylimidazo[1,2-a]pyridin-8-yl] oxymethyl]-2,4-dichlorophenyl]sulfonyl]-2(S)-[[4-[4-[(amino)(hydroxyimino)methyl]benzoyl] piperazin-1-yl]carbonyl]pyrrolidine The expected product is obtained in the form of cream-colored crystals (yield=76%) by following a procedure analogous to Example 4, starting from the compound obtained according to Preparation XV.

M.p.=179–181° C.; $[\alpha]_D^{26}$=−0.7° (c=1.01; $CH_2Cl_2$).

PREPARATION XVI

1-[[3-[[2,3-Dimethylimidazo[1,2-a]pyridin-8-yl] oxymethyl]-2,4-dichlorophenyl]sulfonyl]-2(S)-[[4-[4-[(acetoxyimino)(amino)methyl]benzoyl] piperazin-1-yl]carbonyl]pyrrolidine The expected product is obtained in the form of white crystals (yield=98%) by following a procedure analogous to Preparation X, starting, from the compound obtained according to Example 10.

M.p.=142–145° C.; $[\alpha]_D^{26}$=−13.5° (c=1.05; $CH_2Cl_2$).

EXAMPLE 11

1-[[3-[[2,3-Dimethylimidazo[1,2-a]pyridin-8-yl] oxymethyl]-2,4-dichlorophenyl]sulfonyl]-2(S)-[[4-[4-(aminoiminomethyl)benzoyl]piperazin-1-yl] carbonyl]pyrrolidine The expected product is obtained in the form of white crystals (yield=47%) by following a procedure analogous to Example 5, starting from the compound obtained according to Preparation XVI.

M.p.=170–172° C.; $[\alpha]_D^{21}$=−2.9° (c=1.00; $CH_2Cl_2$).

EXAMPLE 12

1-[[3-[[2,3-Dimethylimidazo[1,2-a]pyridin-8-yl] oxymethyl]-2,4-dichlorophenyl]sulfonyl]-2(S)-[[4-[4-(aminoiminomethyl)benzoyl]piperazin-1-yl] carbonyl]pyrrolidine Dihydrochloride A solution of 736 mg ($1.03.10^{-3}$ mol) of the compound obtained according to Example 11 in 25 ml of dichloromethane is prepared and 650 µl ($2.6.10^{-3}$ mol) of a 4 N solution of hydrogen chloride in dioxane are added. After stirring for 3 hours, the precipitate formed is separated off and taken up with diethyl ether to give a pale yellow solid, which is filtered off. After drying under vacuum, the product is redissolved in water and the solution is filtered and lyophilized to give 710 mg of the expected product in the form of a cream-colored flaky solid (yield=87%).

M.p.=225–229° C.; $[\alpha]_D^{26}$=+19.5° (c=1.07; $CH_3OH$).

EXAMPLE 13

1-[[3-[[2,3-Dimethylimidazo[1,2-a]pyridin-8-yl] oxymethyl]-2,4-dichlorophenyl]sulfonyl]-N-[4-(aminoiminomethyl)phenylmethyl]-2(S)-pyrrolidinecarboxamide A solution of 5 g ($10.1.10^{-3}$ mol) of the compound obtained according to Preparation XII in 100 ml of dimethylformamide is prepared and 2.12 g ($11.10^{-3}$ mol) of EDCI and 1.52 g ($11.10^{-3}$ mol) of HOAT are added. After stirring for one hour at room temperature, this solution is added to a solution of 2.5 g ($11.10^{-3}$ mol) of 4-(aminomethyl) benzenecarboximidamide [or 4-(aminoiminomethyl) benzylamine] dihydrochloride in 100 ml of DMF and 1.2 ml ($11.10^{-3}$ mol) of N-methyl-morpholine. The reaction medium is stirred for 15 hours at room temperature. It is filtered and the filtrate is poured into ethyl ether, with stirring. The precipitate formed in this way is separated off and redissolved in water. Dichloromethane is added and 2 N sodium hydroxide solution is added in order to bring the medium to pH 13. The aqueous and organic phases are separated and the organic phase is washed with water. After drying over magnesium sulfate, the organic phase is concentrated under reduced pressure. The crude product obtained is purified by chromatography on $NH_2$ grafted silica gel using a dichloromethane/ethanol mixture (95/5; v/v) as the eluent to give 3.6 g of the expected product in the form of a white solid (yield=57%).

M.p.=144–146° C.; $[\alpha]_D^{21}$=−34.5° (c=1.03; $CHCl_3$).

EXAMPLE 14

1-[[3-[[2,3-Dimethylimidazo[1,2-a]pyridin-8-yl] oxymethyl]-2,4-dichlorophenyl]sulfonyl]-N-[4-(aminoiminomethyl)phenylmethyl]-2(S)-pyrrolidinecarboxamide Hydrochloride A solution of 0.42 g ($0.66.10^{-3}$ mol) of the compound obtained according to Example 13 in 100 ml of diethyl ether is prepared and 0.75 ml of a 1 N solution of hydrogen chloride in diethyl ether is added, with stirring. The crystals formed are filtered off, washed with ether and dried under vacuum to give the expected product in the form of white crystals (yield=81%).

M.p.=210–214° C.; $[\alpha]_D^{22}$=−12° (c=1.00; $C_2H_5OH$).

PREPARATION XVII

N-[[3-[[3-Bromo-2-methylimidazo[1,2-a]pyridin-8-yl]oxymethyl]-2,4-dichlorophenyl]sulfonyl]-L-proline Methyl Ester A solution of 7 g ($14.10^{-3}$ mol) of the compound obtained according to Preparation I in a mixture of 100 ml of dioxane and 100 ml of ethanol is prepared and 2.5 g ($14.10^{-3}$ mol) of N-bromosuccinimide are added in portions at room temperature, with stirring. After stirring for 1 hour, the solvents are driven off under reduced pressure. The evaporation residue is taken up with dichloromethane and the solution is washed with water and then dried over magnesium sulfate and concentrated under reduced pressure. After purification by chromatography on silica gel using a toluene/2-propanol mixture (97/3; v/v) as the eluent, and recrystallization from 2-propanol, 7.3 g of the expected product (yield=90%) are obtained.

M.p.=146° C.; $[\alpha]_D^{23}$=−17° (c=1.5; $CH_2Cl_2$).

PREPARATION XVIII

N-[[3-[[3-Bromo-2-methylimidazo[1,2-a]pyridin-8-yl]oxymethyl]-2,4-dichlorophenyl]sulfonyl]-L-proline The expected product is obtained in the form of a cream-colored powdery solid (yield=98%) by following a procedure analogous to Preparation II, starting from the compound obtained according to Preparation XVII.

M.p.=145° C.; $[\alpha]_D^{20}$=−30.5° (c=1.05; $CH_2Cl_2$).

PREPARATION XIX

1-[[3-[[3-Bromo-2-methylimidazo[1,2-a]pyridin-8-yl]oxymethyl]-2,4-dichlorophenyl]sulfonyl]-N-[3-[1,1-dimethylethoxycarbonylamino]propyl]-2(S)-pyrrolidinecarboxamide The expected product is obtained in the form of a white solid (yield=95%) by following a procedure analogous to Preparation V, starting from the compound obtained according to Preparation XVIII and (3-aminopropyl)carbamic acid 1,1-dimethylethyl ester [or N-Boc-propanediamine].

M.p.=65° C.; $[\alpha]_D^{22}$=−43° (c=0.44; $CH_3OH$).

PREPARATION XX

1-[[3-[[3-Bromo-2-methylimidazo[1,2-a]pyridin-8-yl]oxymethyl]-2,4-dichlorophenyl]sulfonyl]-N-[3-aminopropyl]-2(S)-pyrrolidinecarboxamide A solution of 0.6 g ($0.83.10^{-3}$ mol) of the compound obtained according to Preparation XIX in 10 ml of dichloromethane is prepared and 89 mg ($0.83.10^{-3}$ mol) of anisole and 3 ml of trifluoroacetic acid are added at 0° C. The reaction mixture is then stirred for 4 hours at room temperatures after which the solvent is driven off under reduced pressure. The residue is taken up with 50 ml of water and the aqueous phase obtained is brought to pH 10 with 1 N sodium hydroxide solution and then extracted with dichloromethane. The organic phase is washed with water, dried over sodium sulfate and then concentrated under reduced pressure to give 0.45 g of the expected product in the form of a white powdery solid.

M.p.=75° C.; $[\alpha]_D^{22}$=−72° (c=0.40; $CH_3OH$).

EXAMPLE 15

1-[[3-[[3-Bromo-2-methylimidazo[1,2-a]pyridin-8-yl]oxymethyl]-2,4-dichlorophenyl]sulfonyl]-N-[3-[4-(aminoiminomethyl)benzoylamino]propyl]-2(S)-pyrrolidinecarboxamide A suspension of 80 mg ($0.4.10^{-3}$ mol) of 4-(aminoiminomethyl)benzoic acid hydrochloride in 6 ml of DMF is prepared and 84 mg ($0.44.10^{-3}$ mol) of EDCI and 60 mg ($0.44.10^{-3}$ mol) of HOAT are added. The mixture is stirred at room temperature for 10 min and 250 mg ($0.40.10^{-3}$ mol) of the compound obtained according to Preparation XX are then added. The reaction mixture is stirred for 20 hours at room temperature and then poured into water. It is extracted with dichloromethane and the resulting organic phase is subsequently washed with saturated sodium bicarbonate solution and then with water. It is dried over sodium sulfate and concentrated under reduced pressure. The crude product is purified by chromatography on $NH_2$ grafted silica gel using a dichloromethane/methanol mixture (98/2; v/v) as the eluent to give 170 mg of the expected product in the form of a white solid (yield=55%).

M.p.=170° C.; $[\alpha]_D^{22}$=−2.6° (c=0.16; $CH_3OH$).

EXAMPLE 16

1-[[3-[[3-Bromo-2-methylimidazo[1,2-a]pyridin-8-yl]oxymethyl]-2,4-dichlorophenyl]sulfonyl]-N-[3-[4-(aminoiminomethyl)benzoylamino]propyl]-2(S)-pyrrolidinecarboxamide Hydrochloride A solution of 153 mg ($0.2.10^{-3}$ mol) of the compound obtained according to Example 15 in 8 ml of ethyl acetate and 2 ml of ethanol is prepared and 0.5 ml of a saturated solution of hydrogen chloride in diethyl ether is added. The mixture is stirred for 10 min and the solvents are then removed under reduced pressure. The residue is then redissolved in water, the solution is filtered and the filtrate is lyophilized to give 120 mg of the expected product in the form of a white powder (yield=75%).

M.p.=200° C.; $[\alpha]_D^{22}$=−13° (c=0.39; $CH_3OH$).

PREPARATION XXI

1-[[3-[[3-Bromo-2-methylimidazo[1,2-a]pyridin-8-yl]oxymethyl]-2,4-dichlorophenyl]sulfonyl]-2(S)-[[4-(1,1-dimethylethoxycarbonyl)piperazin-1-yl]carbonyl]pyrrolidine The expected product is obtained in the form of white crystals (yield=90%) by following a procedure analogous to Preparation XIX, starting from 1-piperazine-carboxylic acid 1-dimethylethyl ester.

M.p.=85° C.; $[\alpha]_D^{22}$=+9.6° (c=1.00; DMSO).

PREPARATION XXII

1-[[3-[[3-Bromo-2-methylimidazo[1,2-a]pyridin-8-yl]oxymethyl]-2,4-dichlorophenyl]sulfonyl]-2(S)-[[piperazin-1-yl]carbonyl]pyrrolidine The expected product is obtained in the form of white crystals (yield=90%) by following a procedure analogous to Preparation XX, starting from the compound obtained according to Preparation XXI.

M.p.=178–180° C.; $[\alpha]_D^{21}$=+16.5° (c=1.01; $CH_3OH$).

EXAMPLE 17

1-[[3-[[3-Bromo-2-methylimidazo[1,2-a]pyridin-8-yl]oxymethyl]-2,4-dichlorophenyl]sulfonyl]-2(S)-[[4-[4-(aminoiminomethyl)benzoyl]piperazin-1-yl]carbonyl]pyrrolidine Hydrochloride The expected product is obtained in the form of pale yellow crystals (yield=40%) by following a procedure analogous to Example 15, starting from the compound obtained according to Preparation XXII, and after purification by reversed phase chromatography on silica gel (grafted silica gel marketed under the name RP18) using an acetonitrile/water/hydrochloric acid mixture (75/25/1; v/v/v) as the eluent.

M.p.=200–204° C.; $[\alpha]_D^{19}$=+21° (c=1.02; $CH_3OH$).

EXAMPLE 18

1-[[3-[[3-Bromo-2-methylimidazo[1,2-a]pyridin-8-yl]oxymethyl]-2,4-dichlorophenyl]sulfonyl]-N-[4-(aminoiminomethyl)phenylmethyl]-2(S)-pyrrolidinecarboxamide A solution of 1.13 g ($2.10^{-3}$ mol) of the compound obtained according to Preparation XVIII in 10 ml of DMF is prepared and 382 mg ($2.10^{-3}$ mol) of EDCI and 272 mg ($2.10^{-3}$ mol) of HOAT are added. The solution is stirred for 20 min at room temperature and then added slowly to a mixture of 453 mg ($2.10^{-3}$ mol) of 4-(aminomethyl)benzenecarboximidamide dihydrochloride and 202 mg ($2.10^{-3}$ mol) of N-methylmorpholine in 10 ml of DMF. The reaction mixture is stirred for 20 hours at room temperature and then poured into 150 ml of water. 1 N sodium hydroxide solution is added, with stirring, in order to bring the medium to pH 13, and the medium is then extracted with dichloromethane. The organic phase is washed and then dried over magnesium sulfate and concentrated under reduced pressure. The product obtained is purified by chromatography on silica gel ($NH_2$ grafted silica gel) using a dichloromethane/methanol mixture (95/5; v/v) as the eluent to give 280 mg of the expected product in the form of a white solid (yield=24%).

M.p.=124° C.; $[\alpha]_D^{25}$=−30° (c=0.57; $CH_3OH$).

EXAMPLE 19

1-[[3-[[3-Bromo-2-methylimidazo[1,2-a]pyridin-8-yl]oxymethyl]-2,4-dichlorophenyl]sulfonyl]-N-[4-(aminoiminomethyl)phenylmethyl]-2(S)-pyrrolidinecarboxamide Hydrochloride The expected product is obtained in the form of a white solid (yield=92%) by following a procedure analogous to Example 16, starting from the compound obtained according to Example 18 (yield=92%).

M.p.=214° C.; $[\alpha]_D^{25}$=−27° (c=0.68; $CH_3OH$).

PREPARATION XXIII

N-[[3-[(2-Methylquinoxalin-8-yl)oxymethyl]-2,4-dichlorolphenyl]sulfonyl]-L-proline Methyl Ester The expected product is obtained in the form of white crystals (yield=92%) by following a procedure analogous to Preparation I, starting from 8-hydroxy-2-methylquinoxaline.

M.p.=158–159° C.; $[\alpha]_D^{24}$=−24.5° (c=1.00; $CHCl_3$).

PREPARATION XXIV

N-[[3-[(2-Methylquinoxalin-8-yl)oxymethly]-2,4-dichlorophenyl]sulfonyl]-L-proline The expected product is obtained in the form of off-white crystals (yield=90%) by following a procedure analogous to Preparation II, starting from the product obtained according to Preparation XXIII.

M.p.=238–240° C.; $[\alpha]_D^{26}$=−111° (c=0.97; $CHCl_3$).

PREPARATION XXV

1-[[3-[(2-Methylquinoxalin-8-yl)oxymethyl]-2,4-dichlorophenyl]sulfonyl]-N-[3-[(4-cyanobenzoyl)amino]propyl]-2(S)-pyrrolidinecarboxamide The expected product is obtained in the form of white crystals (yield=79%) by following a procedure analogous to Preparation V, starting from the product obtained according to Preparation XXIV.

M.p.=104–106° C.; $[\alpha]_D^{26}$=−32° (c=0.96; $CHCl_3$).

EXAMPLE 20

1-[[3-[(2-Methylquinoxalin-8-yl)oxymethyl]-2,4-dichlorophenyl]sulfonyl]-N-[3-[[4-[(amino)(hydroxyimino)methyl]benzoyl]amino]propyl]-2-(S)-pyrrolidinecarboxamide The expected product is obtained in the form of white crystals (yield=88%) by following a procedure analogous to Example 1, starting from the product obtained according to Preparation XXV.

M.p.=172–176° C.; $[\alpha]_D^{23}$=−7.5° (c=0.98; DMSO).

PREPARATION XXVI

1-[[3-[(2-Methylquinoxalin-8-yl)oxymethyl]-2,4-dichlorophenyl]sulfonyl]-N-[3-[[4-[(acetoxyimino)(amino)methyl]benzoyl]amino]propyl]-2(S)-pyrrolidinecarboxamide The expected product is obtained in the form of pinkish crystals (yield=95%) by following a procedure analogous to Preparation VI, starting from the compound obtained according to Example 20.

M.p.=151–154° C.; $[\alpha]_D^{24}$=−10° (c=0.95; DMSO).

EXAMPLE 21

1-[[3-[(2-Methylquinoxalin-8-yl)oxymethyl]-2,4-dichlorophenyl]sulfonyl]-N-[3-[[4-(aminoiminomethyl)benzoyl]amino]propyl]-2(S)-pyrrolidinecarboxamide The expected product is obtained in the form of pinkish crystals (yield=55%) by following, a procedure analogous to Example 2, starting, from the compound obtained according to Preparation XXVI.

M.p.=136–140° C.; $[\alpha]_D^{24}$=−10° (c=1.00; DMSO).

EXAMPLE 22

1-[[3-[(2-Methylquinoxalin-8-yl)oxymethyl]-2,4-dichlorophenyl]sulfonyl]-N-[3-[[4-(aminoiminomethyl)benzoyl]amino]propyl]-2(S)-pyrrolidinecarboxamide Methanesulfonate The expected product is obtained in the form of light yellow crystals (yield=84%) by following a procedure analogous to Example 3, starting from the compound obtained according to Example 21.

M.p.=165–167° C.; $[\alpha]_D^{25}$=−38.2° (c=1.03; $CH_3OH$).

PREPARATION XXVII

1-[[3-[(2-Methylquinoxalin-8-yl)oxymethyl]-2,4-dichlorophenyl]sulfonyl]-2-(S)-[[4-(4-cyanobenzoyl)piperazin-1-yl]carbonyl]pyrrolidine The expected product is obtained in the form white crystals (yield=96%) by following a procedure analogous to Preparation IX, starting from the compound obtained according to Preparation XXIV.

M.p.=126–130° C.; $[\alpha]_D^{26}$=−0.4° (c=1.13; $CHCl_3$).

EXAMPLE 23

1-[[3-[(2-Methylquinoxalin-8-yl)oxymethyl]-2,4-dichlorophenyl]sulfonyl]-2-(S)-[[4-[4-[(amino)(hydroxyimino)methyl]benzoyl]piperazin-1-yl]carbonyl]pyrrolidine The expected product is obtained in the form of white crystals (yield=86%) by following a procedure analogous to Example 4, starting from the compound obtained according to Preparation XXVII.

M.p.=210–212° C.; $[\alpha]_D^{24}$=+19.5° (c=0.47; DMSO).

PREPARATION XXVIII

1-[[3-[(2-Methylquinoxalin-8-yl)oxymethyl]-2,4-dichlorophenyl]sulfonyl]-2(S)-[[4-[4-[(acetoxyimino)(amino)methyl]benzoyl]piperazin-1-yl]carbonyl]pyrrolidine The expected product is obtained in the form of yellow crystals (yield=98%) by following a procedure analogous to Preparation X, starting from the compound obtained according to Example 23.

M.p.=161–165° C.; $[\alpha]_D^{23}$=+9° (c=1.02; DMSO).

EXAMPLE 24

1-[[3-[(2-Methylquinoxalin-8-yl)oxymethyl]-2,4-dichlorophenyl]sulfonyl]-2(S)-[[4-[4-(aminoiminomethyl)benzoyl]piperazin-1-yl]carbonyl]pyrrolidine The expected product is obtained in the form of beige crystals (yield=45%) by following a procedure analogous to Example 5, starting from the compound obtained according to Preparation XXVIII.

M.p.=155–158° C.; $[\alpha]_D^{24}$=+9.7° (c=0.95; DMSO).

EXAMPLE 25

1-[[3-[(2-Methylquinoxalin-8-yl)oxymethyl]-2,4-dichlorophenyl]sulfonyl]-2(S)-[[4-[4-(aminoiminomethyl)benzoyl]piperazin-1-yl]carbonyl]pyrrolidine Hydrochloride The expected product is obtained in the form of a white solid (yield=95%) by following a procedure analogous to Example 16, starting from the compound obtained according to Example 24.

M.p.=192–195° C.; $[\alpha]_D^{24}$=+6.7° (c=1.03, DMSO).

EXAMPLE 26

1-[[3-[(2-Methylquinoxalin-8-yl)oxymethyl]-2,4-dichlorophenyl]sulfonyl]-N-[4-(aminoiminomethyl)phenylmethyl]-2(S)-pyrrolidinecarboxamide The expected product is obtained in the form of a beige solid (yield=27%) by following a procedure analogous to Example 13, starting from the compound obtained according to Preparation XXIV.

M.p.=120–125° C.; $[\alpha]_{D23}$=−42° (c=1.00; CHCl$_3$).

EXAMPLE 27

1-[[3-[(2-Methylquinoxalin-8-yl)oxymethyl]-2,4-dichlorophenyl]sulfonyl]-N-[4-(aminoiminomethyl)phenylmethyl]-2(S)-pyrrolidinecarboxamide Hydrochloride A solution of 387 mg (0.62.10$^{-3}$ mol) of the compound obtained according to Example 26 in 100 ml of ethyl ether is prepared and 0.7 ml of a 1 N solution of hydrogen chloride in ethyl ether is added. The crystals formed are filtered off, washed with ether, dried under vacuum and redissolved in 10 ml of water. After filtration and lyophilization of the filtrate, 376 mg of the expected product are obtained in the form of a white powder (yield=92%).

M.p.=180–184° C.; $[\alpha]_D^{23}$=−43° (c=0.99; ethanol).

PREPARATION XXIX

N-[[3-[[2-Methyl-4H-pyrido[1,2-a]pyrimidin-9-yl-4-one]oxymethyl]-2,4-dichlorophenyl]sulfonyl]-(L)-proline Methyl Ester The expected product is obtained in the form of off-white crystals (yield=56%) by following a procedure analogous to Preparation I, starting from 9-hydroxy-2-methyl-4H-pyrido[1,2-a]pyrimidin-4-one.

M.p.=166° C.; $[\alpha]_D^{22}$=−24° (c=0.37; CHCl$_3$).

PREPARATION XXX

N-[[3-[[2-Methyl-4H-pyrido[1,2-a]pyrimidin-9-yl-4-one]oxymethyl]-2,4-dichlorophenyl]sulfonyl]-(L)-proline The expected product is obtained in the form of a beige solid (yield=92%) by following a procedure analogous to Preparation II, starting from the compound obtained according to Preparation XXIX.

M.p.=150° C.; $[\alpha]_D^{22}$=−86° (c=0.4; CHCl$_3$).

PREPARATION XXXI

1-[[3-[[2-Methyl-4H-pyrido[1,2-a]pyrimidin-9-yl-4-one]oxymethyl]-2,4-dichlorophenyl]sulfonyl]-N-[3-[(4-cyanobenzoyl)amino]propyl]-2(S)-pyrrolidinecarboxamide The expected product is obtained in the form of a white solid (yield=83%) by following a procedure analogous to Preparation V, starting from the compound obtained according to Preparation XXX.

M.p.=112° C.; $[\alpha]_D^{22}$=−50° (c=0.31; CHCl$_3$).

EXAMPLE 28

1-[[3-[[2-Methyl-4H-pyrido[1,2-a]pyrimidin-9-yl-4-one]oxymethyl]-2,4-dichlorophenyl]sulfonyl]-N-3-[4-[(amino)(hydroxyimino)methyl]benzoylamino]propyl]-2(S)-pyrrolidinecarboxamide The expected product is obtained in the form of a white solid (yield=87%) by following a procedure analogous to Example 1, starting from the compound obtained according to Preparation XXXI.

M.p.=251° C.; $[\alpha]_D^{22}$=−11° (c=0.36; DMSO).

PREPARATION XXXII

1-[[3-[[2-Methyl-4H-pyrido[1,2-a]pyrimidin-9-yl-4-one]oxymethyl]-2,4-dichlorophenyl]sulfonyl]-N-[3-[4-](acetoxyimino)(amino)methyl]benzoylamino]propyl]-2(S)-pyrrolidinecarboxamide The expected product is obtained in the form of a creamy white powder (yield=95%) by following a procedure analogous to Preparation VI, starting from the compound obtained according to Example 28.

M.p.=150° C.; $[\alpha]_D^{22}$=−24.5° (c=0.33; CHCl$_3$).

EXAMPLE 29

1-[[3-[[2-Methyl-4H-pyrido[1,2-a]pyrimidin-9-yl-4-one]oxymethyl]-2,4-dichlorophenyl]sulfonyl]-N-[3-[[4-(aminoiminomethyl)benzoyl]amino]propyl]-2(S)-pyrrolidinecarboxamide The expected product is obtained in the form of a white powdery solid (yield=62%) by following a procedure analogous to Example 2, starting from the compound obtained according to Preparation XXXII.

M.p.=153° C.; $[\alpha]_D^{22}$=−19° (c=0.32; DMSO).

EXAMPLE 30

1-[[3-[[2-Methyl-4H-pyrido[1,2-a]pyrimidin-9-yl-4-one]oxymethyl]-2,4-dichlorophenyl]sulfonyl]-N-[3-[[4-(aminoiminomethyl)benzoyl]amino]propyl]-2(S)-pyrrolidinecarboxamide Bis(methanesulfonate)

A solution of 160 mg (0.224.10$^{-3}$ mol) of the compound obtained according to Example 29 in 3 ml of dichloromethane and 3 ml of ethanol is prepared. 43 mg (0.45.10$^{-3}$ mol) of methanesulfonic acid are added and the mixture is stirred for 10 min. 20 ml of diethyl ether are then added and, after 5 min, the crystals formed are filtered off and washed on the filter with ether. After drying under vacuum, the crystals are redissolved in 20 ml of water and the solution is lyophilized to give 170 mg of the expected product in the form of fine white crystals (yield=85%).

M.p.=183° C.; $[\alpha]_D^{24}$=−32° (c=0.46; CH$_3$OH).

PREPARATION XXXIII

1-[4-Cyanobenzoyl]piperazine Trifluoroacetate

A solution of 40.7 g (129.10$^{-3}$ mol) of the compound obtained according to Preparation VII in 500 ml of dichloromethane is prepared and 150 ml of trifluoroacetic acid are added gradually. The mixture is subsequently stirred at room temperature for 30 min and then concentrated under reduced pressure. The residue is taken up with 400 ml of diethyl ether, with stirring; the crystals formed are filtered off and then dried under vacuum to give 30.8 g of the expected product in the form of white crystals (yield=87%).

M.p.=180° C.;

PREPARATION XXXIV 1-(1,1-Dimethylethoxycarbonyl)-2(S)-[[4-(4-cyanobenzoyl)piperazin-1-yl]carbonyl]pyrrolidine A solution of 10.78 g (50.10$^{-3}$ mol) of N-(1,1-dimethylethoxycarbonyl)-L-proline (or N-Boc-L-proline) in 90 ml of DMF is prepared and 11.47 g (60.10$^{-3}$ mol) of EDCI and 8.18 g (60.10$^{-3}$ mol) of HOAT are added. The mixture is stirred for 30 min at room temperature and a solution of 15 g (55.10$^{-3}$ mol) of the compound obtained according to Preparation XXXIII in 90 ml of DMF and 6.08 g (60.10$^{-3}$ mol) of triethylamine is then added. After stirring for 3 hours at room temperature, the reaction medium is poured into iced water and extracted with dichloromethane. The organic phase is washed and then dried over magnesium sulfate and concentrated under reduced pressure. The crude product is purified by chromatography on silica gel using a dichloromethane/methanol mixture (98/2; v/v) as the eluent to give 20 g of the expected product in the form of a white solid (yield=97%).

M.p.=50° C.; $[\alpha]_D^{23}$=+3° (c=0.50; CHCl$_3$).

PREPARATION XXXV

2(S)-[4-(4-Cyanobenzoyl)piperazin-1-ylcarbonyl]pyrrolidine Trifluoroacetate

The expected product is obtained in the form of a white solid (yield=81%) by following a procedure analogous to Preparation XX, starting from the compound obtained according to Preparation XXXIV.

M.p.=50° C.; $[\alpha]_D^{22}$=−35° (c=0.58; CHCl$_3$).

PREPARATION XXXVI

1-[(3-Bromomethyl-2,4-dichlorophenyl)sulfonyl]-2(S)-[[4-(4-cyanobenzoyl)-piperazin-1-yl]carbonyl]pyrrolidine A solution of 13.4 g (39.5.10$^{-3}$ mol) of 3-bromomethyl-2,4-dichlorobenzenesulfonyl chloride in 35 ml of acetonitrile is prepared and 16.9 g (39.5.10$^{-3}$ mol) of the compound obtained according to Preparation XXXV are added at room temperature. A solution of 10 g (0.1 mol) of potassium bicarbonate in 40 ml of water is then added dropwise. The reaction mixture is stirred for 20 hours, water is then added and the mixture is extracted with ethyl acetate. The organic phase obtained is washed with water, dried over magnesium sulfate and concentrated under reduced pressure. The crude product is purified by chromatography on silica gel using a dichloromethane/ethyl acetate mixture (9/1; v/v) as the eluent to give 18.8 g of the expected product (partly containing its chlorinated analog) in the form of a beige solid.

M.p.=115° C.;

PREPARATION XXXVII

1-[[3-[[2-Methylpyrido[1,2-a]pyrimidin-9-yl-4-one]oxymethyl]-2,4-dichlorophenyl]sulfonyl]-2(S)-[[4-(4-cyanobenzoyl)piperazin-1-yl]carbonyl]pyrrolidine The expected product is obtained in the form of white crystals (yield=62%) by following a procedure analogous to Preparation I, starting from 9-hydroxy-2-methylpyrido[1,2-a]pyrimidin-4-one and the compound obtained according to Preparation XXXVI, and after recrystallization from an ethyl acetate/diisopropyl ether mixture.

M.p.=160° C.; $[\alpha]_D^{22}$=+9° (c=0.39; CHCl$_3$).

EXAMPLE 31

1-[[3-[[2-Methylpyrido[1,2-a]pyrimidin-9-yl-4-one]oxymethyl]-2,4-dichlorophenyl]sulfonyl]-2(S)-[[4-[4-[(amino)(hydroxyimino)methyl]benzoyl]piperazin-1-yl]carbonyl]pyrrolidine The expected product is obtained in the form of a white solid (yield=77%) by following a procedure analogous to Example 1, starting from the compound obtained according to Preparation XXXVII.

M.p.=180° C.; $[\alpha]_D^{22}$=+26° (c=0.36; CHCl$_3$).

PREPARATION XXXVIII

1-[[3-[[2-Methylpyrido[1,2-a]pyrimidin-9-yl-4-one]oxymethyl]-2,4-dichlolophenyl]sulfonyl]-2(S)-[[4-[4-[(acetoxyimino)(amino)methyl]benzoyl]piperazin-1-yl]carbonyl]pyrrolidine The expected product is obtained in the form of a white solid (yield=93%) by following a procedure analogous to Preparation VI, starting from the compound obtained according to Example 31.

M.p.=160° C.; $[\alpha]_D^{22}$=+6° (c=0.37; DMSO).

EXAMPLE 32

1-[[3-[[2-Methylpyrido[1,2-a]pyrimidin-9-yl-4-one]oxymethyl]-2,4-dichlorophenyl]sulfonyl]2(S)-[[4-[4-(aminoiminomethyl)benzoyl]piperazin-1-yl]carbonyl]pyrrolidine The expected product is obtained in the form of a yellow solid (yield=44%) by following a procedure analogous to Example 2, starting from the compound obtained according to Preparation XXXVIII.

M.p.=168° C.; $[\alpha]_D^{22}$=+32° (c=0.38; CHCl$_3$).

EXAMPLE 33

1-[[3-[[2-Methylpyrido[1,2-a]pyrimidin-9-yl-4-one]oxymethyl]-2,4-dichlorophenyl]sulfonyl]-2(S)-[[4-[4-(aminoiminoethyl)benzoyl]piperazin-1-yl-carbonyl]pyrrolidine Bis(methanesulfonate)

The expected product is obtained in the form of a white solid (yield=80%) by following a procedure analogous to Example 30, starting from the compound obtained according to Example 32.

M.p.=181° C.; $[\alpha]_D^{24}$=+13° (c=0.35; CH$_3$OH).

PREPARATION XXXIX

N-[[3-[(2,4-Dimethylquinazolin-8-yl)oxymethyl]-2,4-dichlorophenyl]sulfonyl]-L-proline Methyl Ester The expected product is obtained in the form of a white solid (yield=70%) by following a procedure analogous to Preparation I, starting from 2,4-dimethyl-8-hydroxyquinazoline.

M.p.=140–142° C.; $[\alpha]_D^{24}$=−29° (c=1; CHCl$_3$).

PREPARATION XL

N-[[3-[(2,4-Dimethylquinazolin-8-yl)oxymethyl]-2,4-dichlorophenyl]sulfonyl]-L-proline The expected product is obtained in the form of a beige solid (yield=98%) by following a procedure analogous to Preparation II, starting from the compound obtained in Preparation XXXIX.

M.p.=94–96° C.;

EXAMPLE 34

1-[[3-[(2,4-Dimethylquinazolin-8-yl)oxymethyl]-2,4-dichlorophenyl]sulfonyl]-N-[4-(aminoimiomethyl)phenylmethyl]-2(S)-pyrrolidinecarboxamide The expected product is obtained in the form of a white powder (yield=25%) by following a procedure analogous to Example 13, starting from the compound obtained in Preparation XL.

M.p.=139–142° C.;

EXAMPLE 35

1-[[3-[(2,4-Dimethylquinazolin-8-yl)oxymethyl-2,4-dichlorophenyl]sulfonyl]-N-[4-(aminoiminomethyl)phenylmethyl]2(S)-pyrrolidinecarboxamide Hydrochloride The expected product is obtained in the form of a white powder (yield=95%) by following a procedure analogous to Example 16, starting from the compound obtained according to Example 34.

M.p.=177–179° C.; $[\alpha]_D^{21}$=−43° (c=0.80; CH$_3$OH).

PREPARATION XLI

N-[[3-[[3-Chloro-2-methylimidazo[1,2-a]pyridin-8-yl]oxymethyl]-2,4-dichlorophenyl]sulfonyl]-L-proline Methyl Ester The expected product is obtained in the form of a beige solid (yield=95%) by following a procedure analogous to Preparation XVII, the N-bromosuccinimide being replaced with N-chlorosuccinimide.

M.p.=60° C.; $[\alpha]_D^{22}$=+13° (c=0.35; DMSO).

PREPARATION XLII

N-[[3-[[3-Chloro-2-methylimidazo[1,2-a]pyridin-8-yl]oxymethyl]-2,4-dichlorophenyl]sulfonyl]-L-proline The expected product is obtained in the form of a white solid (yield=88%) by following a procedure analogous to Preparation XVIII, starting from the compound obtained according to Preparation XLI.

M.p.=144° C.; $[\alpha]_D^{22}$=−60.5° (c=0.35; CHCl$_3$).

PREPARATION XLIII

1-[[3-[[3-Chloro-2-methylimidazo[1,2-a]pyridin-8-yl]oxymethyl]-2,4-dichlorophenyl]sulfonyl]-N-[3-[(4-cyanobenzoyl)amino]propyl]-2(S)-pyrrolidinecarboxamide The expected product is obtained in the form of an off-white solid (yield=51%) by following a procedure analogous to Preparation V, starting from the compound obtained in Preparation XLII.

M.p.=115° C.; $[\alpha]_D^{22}$=−32° (c=0.60; CHCl$_3$).

EXAMPLE 36

1-[[3-[[3-Chloro-2-methylimidazo[1,2-a]pyridin-8-yl]oxymethyl]-2,4-dichlorophenyl]sulfonyl]-N-[3-[[4-[(amino)(hydroxyimino)methyl]benzoyl]amino]propyl]-2(S)-pyrrolidinecarboxamide The expected product is obtained in the form of a white solid (yield=96%) by following a procedure analogous to Example 1, starting from the compound obtained in Preparation XLIII.

M.p.=155° C.; $[\alpha]_D^{22}$=−41° (c=0.40; CHCl$_3$).

PREPARATION XLIV

1-[[3-[[3-Chloro-2-methylimidazo[1,2-a]pyridin-8-yl]oxymethyl]-2,4-dichlorophenyl]sulfonyl]-N-[3-[[4-[(acetoxyimino)(amino)methyl]benzoyl]amino]propyl]-2(S)-pyrrolidinecarboxamide The expected product is obtained in the form of a crude solid (yield=82%) by following a procedure analogous to Preparation VI, starting from the compound obtained according to Example 36.

M.p.=170° C.; $[\alpha]_D^{21}$=−32° (c=0.35; CHCl$_3$).

EXAMPLE 37

1-[[3-[[3-Chloro-2-methylimidazo[1,2-a]pyridin-8-yl]oxymethyl]-2,4-dichlorophenyl]sulfonyl]-N-[3-[[4-(aminoiminomethyl)benzoyl]amino]propyl]-2(S)-pyrrolidinecarboxamide The expected product is obtained in the form of a beige solid (yield=47%) by following a procedure analogous to Example 2, starting from the compound obtained in Preparation XLIV.

M.p.=115° C.; $[\alpha]_D^{22}$=−9.5° (c=0.55; DMSO).

EXAMPLE 38

1-[[3-[[3-Chloro-2-methylimidazo[1,2-a]pyridin-8-yl]oxymethyl]-2,4-dichlorophenyl]sulfonyl]-N-[3-[[4-(aminoimiomethyl)benzoyl]amino]propyl]-2(S)-pyrrolidinecarboxamide Bis(methanesulfonate)

The expected product is obtained in the form of a white solid (yield=90%) by following a procedure analogous to Example 30, starting from the compound obtained according to Example 37.

M.p.=154° C.; $[\alpha]_D^{27}$=−19° (c=0.32; CH$_3$OH).

PREPARATION XLV

1-[[3-[[3-Chloro-2-methylidazo[1,2-a]pyridin-8-yl]
oxymethyl]-2,4-dichlorophenyl]sulfonyl]-2(S)-[[4-
(4-cyanobenzoyl)piperazin-1-yl]carbonyl]pyrrolidine The expected product is obtained in the form of a creamy white solid (yield=49%) by following a procedure analogous to Preparation V, starting from the compounds obtained according to Preparations XLII and VIII.

M.p.=100° C.; $[\alpha]_D^{28}$=−11° (c=0.35; CH$_3$OH).

EXAMPLE 39

1-[[3-[[3-Chloro-2-methylimidazo[1,2-a]pyridin-8-
yl]oxymethyl]]-2,4-dichlorophenyl]sulfonyl]-2(S)-
[[4-[4-[(amino)(hydroxyimino)methyl]benzoyl]
piperazin-1-yl]carbonyl]pyrrolidine The expected product is obtained in the form of a white solid (yield=96%) by following a procedure analogous to Example 1, starting from the compound obtained according to Preparation XLV.

M.p.=168° C.; $[\alpha]_D^{28}$=−25° (c=0.59; CH$_3$OH).

PREPARATION XLVI

1-[[3-[[3-Chloro-2-methylimidazo[1,2-a]pyridin-8-
yl]oxymethyl]-2,4-dichlorophenyl]sulfonyl]-2(S)-
[[4-[4-[(acetoxyimino)(amino)methyl]benzoyl]
piperazin-1-yl]carbonyl]pyrolidine The expected product is obtained in the form of an off-white solid (yield=88%) by following a procedure analogous to Preparation VI, starting from the compound obtained according to Example 39.

M.p.=150° C.; $[\alpha]_D^{26}$=−16.5° (c=0.40; CH$_3$OH).

EXAMPLE 40

1-[[3-[[3-Chloro-2-methylimidazo[1,2-a]pyridin-8-
yl]oxymethyl]-2,4-dichlorophenyl]sulfonyl]-2(S)-
[[4-[4-[(aminoiminomethyl)benzoyl]piperazin-1-yl]
carbonyl]pyrrolidine The expected product is obtained in the form of a pale yellow solid (yield=96%) by following a procedure analogous to Example 2, starting from the compound obtained according to Preparation XLVI.

M.p.=164° C.; $[\alpha]_D^{26}$=−14° (c=0.33; CH$_3$OH).

EXAMPLE 41

1-[[3-[[3-Chloro-2-methylimidazo[1,2-a]pyridin-8-
yl]oxymethyl]-2,4-dichlorophenyl]sulfonyl]-2(S)-
[[4-[4-[(aminoiminomethyl)benzoyl]piperazin-1-yl]
carbonyl]pyrrolidine Bis(methanesulfonate)

The expected product is obtained in the form of a fine white solid (yield=83%) by following a procedure analogous to Example 3 (in this case dichloromethane is used to dissolve the starting compound), starting from the compound obtained according to Example 40.

M.p.=192° C.; $[\alpha]_D^{27}$=+21° (c=0.42; CH$_3$OH).

PREPARATION XLVII

N-[[3-[(2-Aminopyridin-3-yl)oxymethyl]-2,4-
dichlorophenyl]sulfonyl]-(L)-proline Methyl Ester A solution of 4 g (36.4.10$^{-3}$ mol) of 2-amino-3-hydroxypyridine in 200 ml of dimethylformamide is prepared and 1.09 g (36.4.10$^{-3}$ mol) of sodium hydride are added at room temperature. After stirring for 30 min. 15.7 0, (36.4.10$^{-3}$ mol) of N-[(3-bromomethyl-2,4-dichlorophenyl) sulfonyl]-(L)-proline methyl ester are added and the mixture is stirred for 2 hours at room temperature. The reaction medium is then poured into 250 ml of iced water. The product is filtered off and redissolved in ethyl acetate. The solution is washed with water and then dried over sodium sulfate and concentrated under reduced pressure. The crude product obtained is purified by chromatography on silica gel using a dichloromethane/methanol mixture (97/3; v/v) as the eluent to give 12.4 g of the expected compound in the form of orange-yellow crystals (yield=74.5%).

M.p.=68° C.; $[\alpha]_D^{25}$=−12.8° (c=1.05; CH$_3$OH).

PREPARATION XLVIII

N-[[3-[[3-Acetyl-2-methylimidazo[1,2-a]pyridin-8-
yl]oxymethyl]-2,4-dichlorophenyl]sulfonyl]proline
Methyl Ester A solution of 10.1 g (22.10$^{-3}$ mol) of the compound obtained according to Preparation XLVII in 160 ml of ethanol is prepared. 6 ml (50.10$^{-3}$ mol) of 3-chloro-2,4-pentanedione are added, with stirring, and the reaction mixture is stirred at the reflux point of the solvent for 15 hours. It is then concentrated under reduced pressure and the crude product obtained is purified by chromatography on silica gel using a methylcyclohexane/ethyl acetate mixture (1/1; v/v) as the eluent to give 2.67 g of the expected product in the form of beige crystals (yield=22.5%).

M.p.=178° C.; $[\alpha]_D^{25}$=−8.6° (c=1.05; DMSO).

PREPARATION IL

N-[[3-[[3-Acetyl-2-methylimidazol[1,2-a]pyridin-8-
yl]oxymethyl]-2,4-dichlorophenyl]sulfonyl]proline The expected product is obtained in the form of creamy white crystals (yield=91%) by following a procedure analogous to Preparation II, starting from the compound obtained according to Preparation XLVIII.

M.p.=162–164° C.; $[\alpha]_D^{25}$=−8.3° (c=1.01; CH$_3$OH).

PREPARATION L

1-[[3-[[3-Acetyl-2-methylimidazo[1,2-a]pyridin-8-
yl]oxymethyl]-2,4-dichlorophenyl]sulfonyl]-N-[3-
[(4-cyanobenzoyl)amino]propyl]-2(S)-
pyrrolidinecarboxamide The expected product is obtained in the form of off-white crystals (yield=94%) by following a procedure analogous to Preparation V, starting from the compound obtained in Preparation IL.

M.p.=100–102° C.; $[\alpha]_D^{20}$=−30.6° (c=1.02; CHCl$_3$).

EXAMPLE 42

1-[[3-[[3-Acetyl-2-methylimidazo[1,2-a]pyridin-8-
yl]oxymethyl]-2,4-dichlorophenyl]sulfonyl]-N-[3-
[[4-[(amino)(hydroxyimino)methyl]benzoyl]amino]
propyl]-2(S)-pyrrolidinecarboxamide The expected product is obtained in the form of white crystals (yield=88%) by following a procedure analogous to Example 1, starting from the compound obtained in Preparation L.

M.p.=164–166° C.; $[\alpha]_D^{25}$=−22° (c=1.00; CH$_3$OH).

PREPARATION LI

1-[[3-[[3-Acetyl-2-methylimidazo[1,2-a]pyridin-8-yl]oxymethyl]-2,4-dichlorophenyl]sulfonyl]-N-[3-[[4-[(acetoxyimino)(amino)methyl]benzoyl]amino]propyl]-2(S)-pyrrolidinecarboxamide The expected product is obtained in the form of white crystals (yield=97%) by following a procedure analogous to Preparation VI, starting from the compound obtained according to Example 42.

M.p.=115–117° C.; $[\alpha]_D^{24}$=−6.4° (c=1.06; DMSO).

EXAMPLE 43

1-[[3-[[3-Acetyl-2-methylimidazo[1,2-a]pyridin-8-yl]oxymethyl]-2,4-dichlorophenyl]sulfonyl]-N-[3-[[4-(aminoiminomethyl)benzoyl]amino]propyl]-2(S)-pyrrolidinecarboxamide The expected product is obtained in the form of white crystals (yield=69%) by following a procedure analogous to Example 2, starting from the compound obtained in Preparation LI.

M.p.=158–160° C.; $[\alpha]_D^{21}$=−9.5° (c=1.01; DMSO).

EXAMPLE 44

1-[[3-[[3-Acetyl-2-methylimidazo[1,2-a]pyridin-8-yl]oxymethyl]-2,4-dichlorophenyl]sulfonyl]-N-[3-[[4-(aminoiminomethyl)benzoyl]amino]propyl]-2(S)-pyrrolidinecarboxamide Bis(methanestilfonate)

The expected product is obtained in the form of white crystals (yield=84%) by following a procedure analogous to Example 3, starting from the compound obtained according to Example 43.

M.p.=170–172° C.; $[\alpha]_D^{22}$=−7.5° (c=1.02; DMSO).

The activity of the products according to the invention was evaluated in respect of their ability to bind to the bradykinin receptors. Kinins, of which bradykinin is the main representative, actually form a group of small peptides which make an important contribution to the inflammatory response and therefore appear to be involved in the pathophlysiology of inflammatory diseases. Furthermore, bradykinin is one of the most potent analgesics known. Kinins activate two types of receptor, called $B_1$ and $B_2$. The $B_2$ receptor belongs to the large family of receptors with seven transmembrane domains coupled to the G proteins. In the present invention we describe compounds which bind to the $B_2$ receptor and thereby block the binding of bradykinin.

The following pharmacological test is used: Ileum segments are isolated from male guinea-pigs [of the Dunkin-Hartley strain (Iffa Credo, l'Arbresle, France)] and ground in the following TES buffer: TES 25 mM, 1,10-phenanthroline 1 mM (pH 6.8), bacitracin 140 µg/ml, BSA 1 g/l. The membranes are then isolated by centrifugation (18,000 rpm; 20 min 4° C.). The binding studies are carried out in this TES buffer using [$^3$H]-bradykinin (120 pM) and 50 µg of membrane protein per test (final volume 500 µl) with an equilibrium time of 90 min at 20° C. The percentage inhibition of the binding of [$^3$H]-bradykinin is then determined in the presence of one of the test compounds according to the invention at a concentration of $10^{-6}$ M.

The results obtained from these tests (shown as "activity") are collated in Table I below with reference to the Examples given in the description. In this Table, the meaning of the heterocyclic radicals Q is given in the notes and the nature of the salts is indicated by the abbreviations Chl in the case of a hydrochloric acid salt and Ms in the case of a methanesulfonic acid salt.

The compounds according to the invention have an antagonistic effect towards the bradykinin $B_2$ receptor (they inhibit the activation of the $B_2$ receptors which is induced by bradykinin). This property has been demonstrated experimentally by means of pharmacological tests described in the publication by D. PRUNEAU et al. (British Journal of Pharmacology, October 1995, vol. 116 (no. 3), pp. 2106–2112) and performed on guilnea-pig ileum. The experimental results, evaluated by the $pK_B$ described in the above publication, are reported in the summary Table.

The compounds of the present invention which inhibit the binding of [$^3$H]-bradykinin to the guinea-pig $B_2$ receptor (see Table I) also bind to the human $B_2$ receptor cloned and transfected in a stable manner into CHO cells (Chinese Hamster Ovary cells). Thus, in this test, some compounds inhibit the binding of [$^3$H]-bradykinin to the $B_2$ receptor by at least 95% at a concentration of 10 µM.

The compounds of the present invention can be useful in the treatment of pain and particularly in the treatment of numerous pathological conditions involving bradykinin or its homologs. These pathological conditions include septic and hemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angioedema, migraine, encephalomyelitis, meningitis, cerebrovascular complications (especially those caused by cerebral traumatic shock), certain neurological disorders, vascular inflammatory states (for example atherosclerosis and arteritis of the lower limbs), painful states (for example headache, toothache, menstrual pain), premature uterine contractions, cystitis and burns. The compounds according to the invention can also be useful for the potentiation of antiviral agents.

The compounds of the present invention, which can be used in the form of the free base or in the form of their non-toxic addition salts in association with a physiologically acceptable excipient, are generally prescribed in human therapeutics at doses of about 1 to 1000 mg/day in a form which can be administered orally, by intravenous, intramuscular or subcutaneous injection, transdermally, by means of aerosols or by means of suppositories.

These compounds can also be administered topically, for example in the form of a gel or ointment.

The compounds of the present invention are also useful as pharmacological reagents, especially for the study of hormone-receptor interactions. Use as a pharmacological reagent may require a radiolabeled derivative of one of the compounds according to the invention (for example with tritium [$^3$H] or sulfur [$^{35}$S]) in order to obtain a radioligand intended for conformational studies of the bradykinin $B_2$ receptor or for binding tests involving this type of receptor, for example for the evaluation of novel compounds which are capable of exhibiting an affinity for the bradykinin $B_2$ receptor.

TABLE I

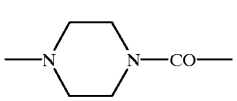

| Ex. | Q | $R_1$ | A | $R_2$ | Salt | Activity % | $pK_B$ |
|---|---|---|---|---|---|---|---|
| 1 | Het 1 | H | —NH—(CH$_2$)$_3$—NH—CO— | OH | — | | |
| 2 | Het 1 | H | —NH—(CH$_2$)$_3$—NH—CO— | H | — | | |
| 3 | Het 1 | H | —NH—(CH$_2$)$_3$—NH—CO— | H | Ms | | |
| 4 | Het 1 | H | 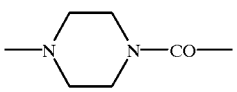 | OH | — | | |
| 5 | Het 1 | H | 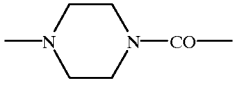 | H | — | | |
| 6 | Het 1 | H | 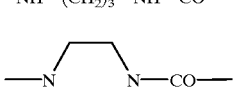 | H | Ms | | |
| 7 | Het 1 | CH$_3$ | —NH—(CH$_2$)$_3$—NH—CO— | OH | — | | |
| 8 | Het 1 | CH$_3$ | —NH—(CH$_2$)$_3$—NH—CO— | H | — | | |
| 9 | Het 1 | CH$_3$ | —NH—(CH$_2$)$_3$—NH—CO— | H | Ms | 97.4 | 8.6 |
| 10 | Het 1 | CH$_3$ | 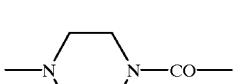 | OH | — | | |
| 11 | Het 1 | CH$_3$ | 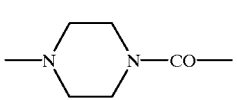 | H | — | | |
| 12 | Het 1 | CH$_3$ | 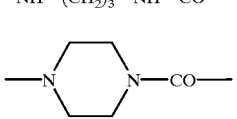 | H | Chl | | |
| 13 | Het 1 | CH$_3$ | —NH—CH$_2$— | H | — | | |
| 14 | Het 1 | CH$_3$ | —NH—CH$_2$— | H | Chl | | |
| 15 | Het 1 | Br | —NH—(CH$_2$)$_3$—NH—CO— | H | — | | |
| 16 | Het 1 | Br | —NH—(CH$_2$)$_3$—NH—CO— | H | Chl | 100 | 9.1 |
| 17 | Het 1 | Br | piperazine-CO | H | Chl | 100 | 8.4 |
| 18 | Het 1 | Br | —NH—CH$_2$— | H | — | | |
| 19 | Het 1 | Br | —NH—CH$_2$— | H | Chl | | |
| 20 | Het 2 | — | —NH—(CH$_2$)$_3$—NH—CO— | OH | — | | |
| 21 | Het 2 | — | —NH—(CH$_2$)$_3$—NH—CO— | H | — | | |
| 22 | Het 2 | — | —NH—(CH$_2$)$_3$—NH—CO— | H | Ms | 97.5 | 8.4 |

TABLE I-continued

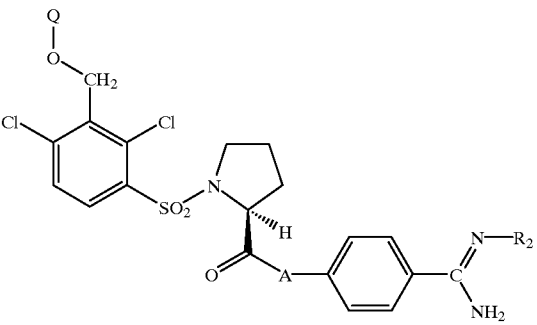

| Ex. | Q | R₁ | A | R₂ | Salt | Activity % | pK$_B$ |
|---|---|---|---|---|---|---|---|
| 23 | Het 2 | — | —N(piperazine)N—CO— | OH | | | |
| 24 | Het 2 | — | —N(piperazine)N—CO— | H | | | |
| 25 | Het 2 | — | —N(piperazine)N—CO— | H | Chl | | |
| 26 | Het 2 | — | —NH—CH₂— | H | — | | |
| 27 | Het 2 | — | —NH—CH₂— | H | Chl | | |
| 28 | Het 3 | — | —NH—(CH₂)₃—NH—CO— | OH | — | | |
| 29 | Het 3 | — | —NH—(CH₂)₃—NH—CO— | H | — | | |
| 30 | Het 3 | — | —NH—(CH₂)₃—NH—CO— | H | Ms | 99.3 | 7.9 |
| 31 | Het 3 | — | —N(piperazine)N—CO— | OH | — | | |
| 32 | Het 3 | — | —N(piperazine)N—CO— | H | — | | |
| 33 | Het 3 | — | —N(piperazine)N—CO— | H | Ms | 96 | 7.8 |
| 34 | Het 4 | — | —NH—CH₂— | H | — | | |
| 35 | Het 4 | — | —NH—CH₂— | H | Chl | | |
| 36 | Het 1 | Cl | —NH—(CH₂)₃—NH—CO— | OH | — | | |
| 37 | Het 1 | Cl | —NH—(CH₂)₃—NH—CO— | H | — | | |
| 38 | Het 1 | Cl | —NH—(CH₂)₃—NH—CO— | H | Ms | 100 | |
| 39 | Het 1 | Cl | —N(piperazine)N—CO— | OH | — | | |

TABLE I-continued
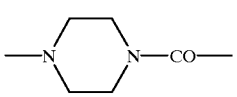
| Ex. | Q | R₁ | A | R₂ | Salt | Activity % | $pK_B$ |
|---|---|---|---|---|---|---|---|
| 40 | Het 1 | Cl | —N∩N—CO— | H | — | | |
| 41 | Het 1 | Cl | —N∩N—CO— | H | Ms | 100 | |
| 42 | Het 1 | —CO—CH₃ | —NH—(CH₂)₃—NH—CO— | OH | — | | |
| 43 | Het 1 | —CO—CH₃ | —NH—(CH₂)₃—NH—CO— | H | — | | |
| 44 | Het 1 | —CO—CH₃ | —NH—(CH₂)₃—NH—CO— | H | Ms | 100 | |
Notes:
Het 1 = 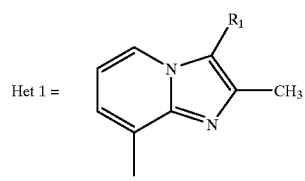
Het 2 = 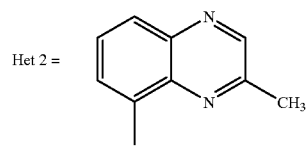
Het 3 = 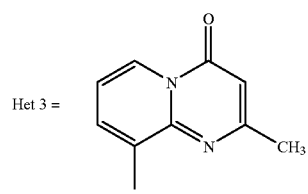
Het 4 = 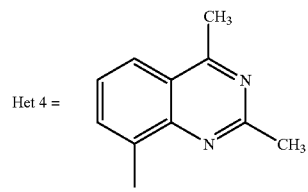
Ms: addition salt with methanesulfonic acid
Chl: addition salt with hydrochloric acid

What is claimed is:

1. An [N-(Benzenesulfonyl)]N-(benzenesulfonyl)-L-proline compound selected from the group consisting of:

(i) the compounds of formula I:

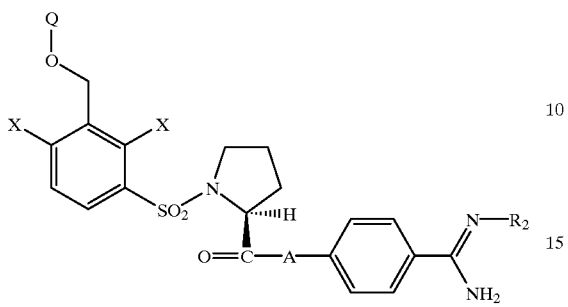

(I)

in which:

X is a halogen atom,

A is a divalent group

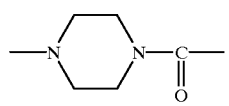

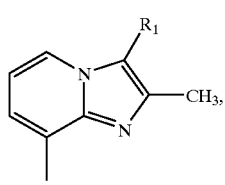

Q is a group

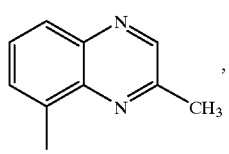

(Het 1)

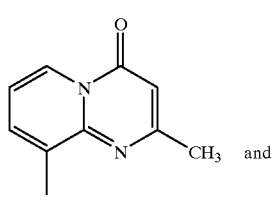

(Het 2)

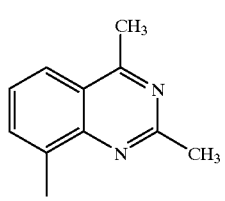

(Het 3)

(Het 4)

$R_1$ is a hydrogen atom, a halogen atom, a $C_1$–$C_3$ alkyl group with a linear or branched hydrocarbon chain, or a $C_1$–$C_5$ 1-oxoalkyl group, $R_2$ is a hydrogen atom or an OH group, and n is 2, 3 or 4; and (ii) their addition salts.

2. The compound according to claim 1, wherein X is Cl.

3. A therapeutic composition which contains, in association with a physiologically acceptable excipient, at least one compound selected from the group consisting of the compounds of formula I and their non-toxic addition salts according to claim 1.

4. A method for the preparation of a compound of formula I:

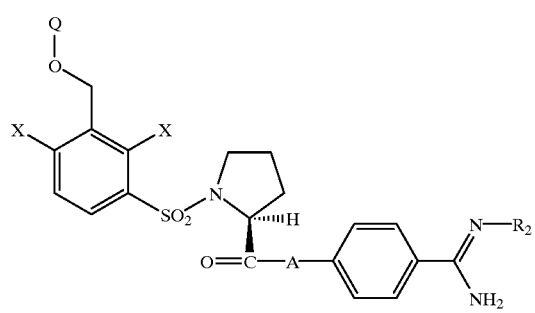

(I)

in which:

X is a halogen atom,

A is a divalent group

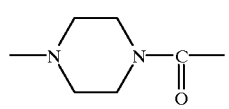

Q is a group selected from the group consisting of

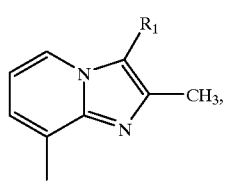

(Het 1)

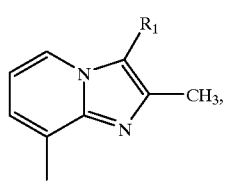

(Het 2)

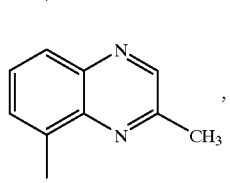

(Het 3)

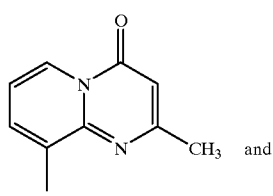

and

-continued

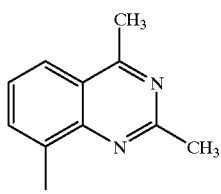
(Het 4)

R$_1$ is a hydrogen atom, a halogen atom, or a C$_1$–C$_3$ alkyl group with a linear or branched hydrocarbon chain, R$_2$ is H, or its addition salts, said method comprising:

(1) reacting an alkali metal salt of a hydroxylated heterocyclic compound of the formula Q-O-Met in which:

Met is an alkali metal, and

Q is a heterocyclic group selected from the group consisting of Het 1, Het 2, Het 3 and Het 4:

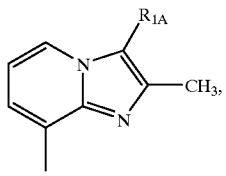
(Het 1)

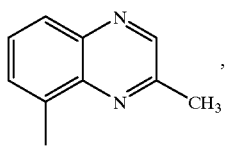
(Het 2)

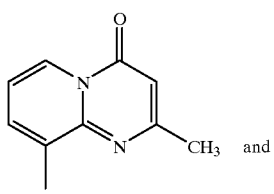
(Het 3)

and

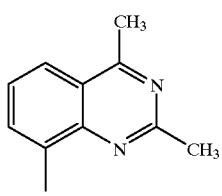
(Het 4)

R$_{1A}$ being a hydrogen atom or a C$_1$–C$_3$ alkyl group, with a compound of the formula II:

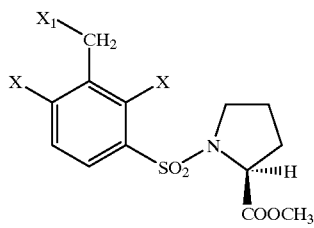
(II)

in which X is a halogen atom and X$_1$ is a halogen atom, in an anhydrous solvent, at a temperature of between 0 and 50° C., for 0.5 to 10 hours, to give a compound of the formula III:

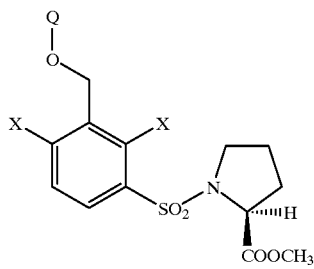
(III)

in which Q, X and R$_{1A}$ are as defined above;

(2) optionally, when Q in the compound of formula III is Het 1 and R$_{1A}$ is a hydrogen atom, reacting said compound of the formula III with a halogenating agent in a solvent, at a temperature of between about 0 and 50° C., for 0.5 to 20 hours, to give a compound of the formula III':

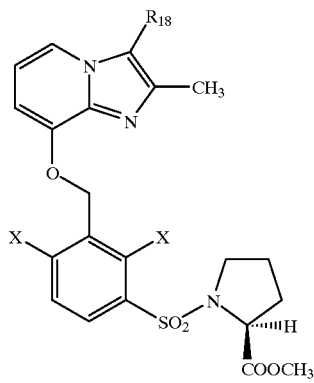
(III')

in which:

R$_{1B}$ is a halogen atom, (3) hydrolyzing the ester group of the compound of the formula III or III' at a temperature of from 20 to 60° C., for 1 to 5 hours, to give a compound of the formula IV:

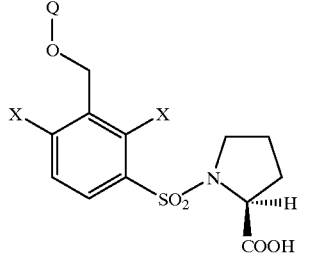
(IV)

in which Q and X are as defined above and R1 is a hydrogen atom, a halogen atom or a C$_1$–C$_3$ alkyl group; and (4) reacting the compound of the formula IV with the salt of an amine of the formula

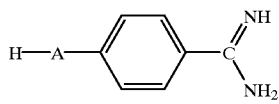
(V)

wherein A is a group

—NH—(CH$_2$)$_n$—NH—CO—, —NH—CH$_2$—or

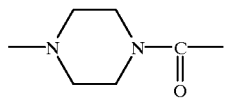

in which n is 2, 3 or 4,
in a solvent, at a temperature between 10–35° C., for 2 to 50 hours, to give the compound of the formula I.

5. The method of claim 4, further comprising reacting the compound of the formula I, thus obtained, with an acid to give a corresponding acid addition salt.

6. A method for the preparation of a compound of the formula I:

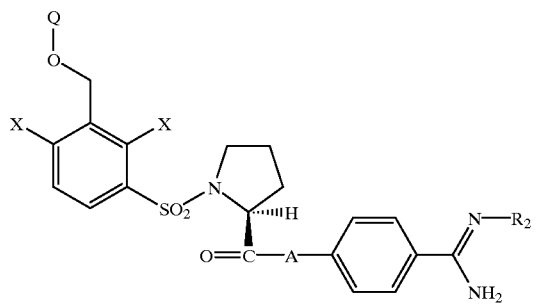
(I)

in which:
X is a halogen atom,
A is a divalent group

—NH—(CH$_2$)$_n$—NH—CO—, —NH—CH$_2$—or

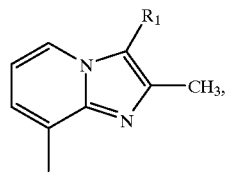

Q is a group selected from the group consisting of

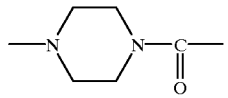
(Het 1)

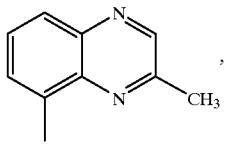
(Het 2)

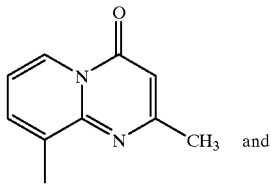
(Het 3)

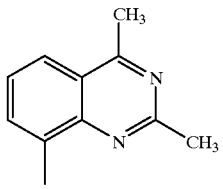
(Het 4)

$R_1$ is a hydrogen atom, a halogen atom, or a $C_1$–$C_3$ alkyl group with a linear or branched hydrocarbon chain, and
$R_2$ is OH or H,
or its addition salts,
said method comprising:

(1) reacting an alkali metal salt of a hydroxylated heterocyclic compound of the formula Q-O-Met in which:
Met is an alkali metal, and
Q is a heterocyclic group selected from the group consisting of Het 1, Het 2, Het 3 and Het 4:

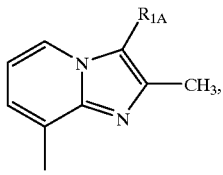
(Het 1)

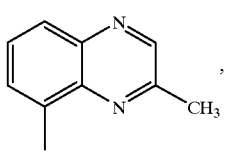
(Het 2)

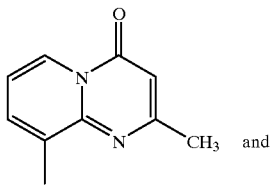
(Het 3)

(Het 4)

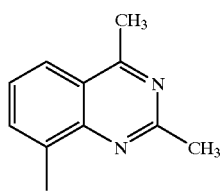

$R_{1A}$ being a hydrogen atom or a $C_1$–$C_3$ alkyl group, with a compound of the formula II:

(II)

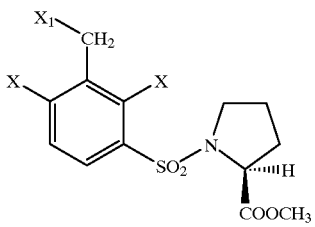

in which X is a halogen atom and $X_1$ is a halogen atom, in an anhydrous solvent, at a temperature of between 0 and 50° C., for 0.5 to 10 hours, to give a compound of the formula III:

(III)

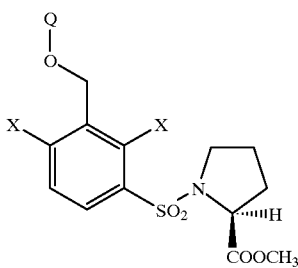

in which Q, X and $R_{1A}$ are as defined above;

(2) optionally, when Q in the compound of formula III is Het 1 and $R_{1A}$ is a hydrogen atom, reacting said compound of the formula III with a halogenating agent in a solvent, at a temperature of between 0 and 50° C., for 0.5 to 20 hours, to give a compound of the formula III':

(III')

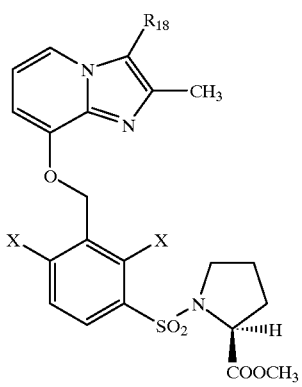

in which $R_{1B}$ is a halogen atom, (3) hydrolyzing the ester group of the compound of the formula III or III' at a temperature of from 20 to 60° C., for 1 to 5 hours, to give a compound of the formula IV:

(IV)

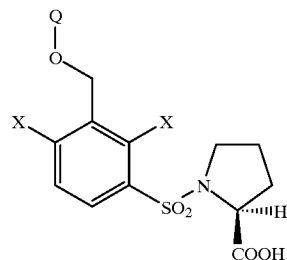

in which Q and X are as defined above and $R_1$ is a hydrogen atom, a halogen atom or a $C_1$–$C_3$ alkyl group;

(4) reacting the acid compound of the formula IV in which $R_1$ is a hydrogen atom, a chlorine atom or a $C_1$–$C_3$ alkyl group with a linear or branched hydrocarbon chain, with a compound of the formula VI:

(VI)

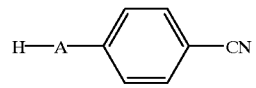

in which A is a group $$-NH-(CH_2)_n-NH-CO-, \quad -NH-CH_2- \text{ or}$$

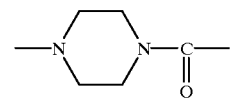

in which n is 2, 3 or 4, in a solvent, at a temperature between 10–35° C., for 2 to 50 hours, to give a compound of the formula VII:

(VII)

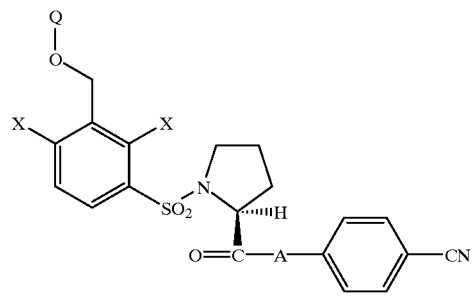

in which Q, $R_1$, X and A are as defined above;

(5) reacting the compound of the formula VII with hydroxylamine in a solvent, at a temperature between 15–25° C., for 1 to 12 hours, to give a compound of the formula VIII:

(VIII)

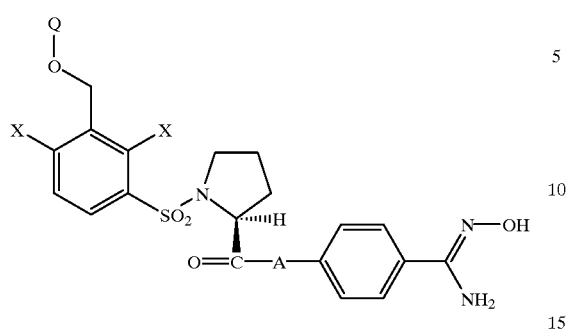

in which Q, $R_1$, X and A are as defined above, said compound VIII being a compound of the formula I wherein $R_2$ is OH;

(6) acetylating the compound of the formula VIII at a temperature between 10–35° C., for 1 to 8 hours, to give a compound of the formula IX:

(IX)

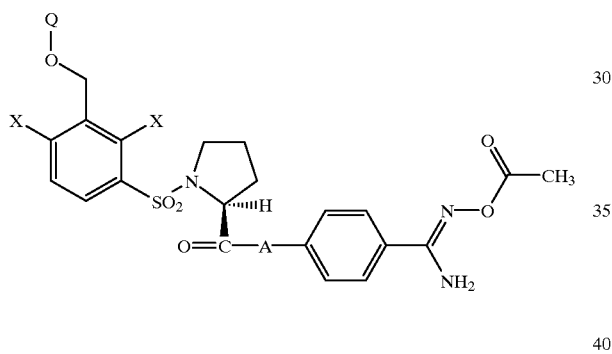

in which Q, $R_1$, X and A are as defined above; and (7) reducing the compound of the formula IV, thus obtained, by catalytic hydrogenation, at a temperature between 10–35° C., under a hydrogen pressure of between $10^5$ and $10^6$ Pascals, to give the compound of the formula I in which Q, $R_1$, X and A are as defined above and $R_2$ is H.

7. A method for the preparation of a compound of the formula I:

(I)

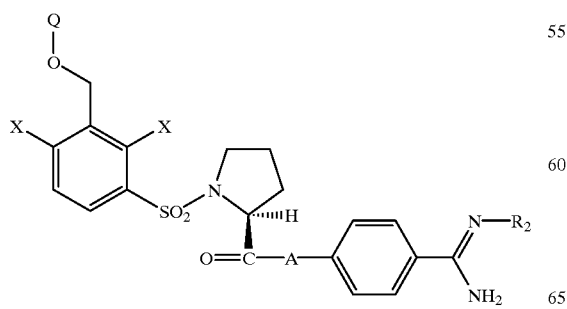

in which

X is a halogen atom,

A is a divalent group

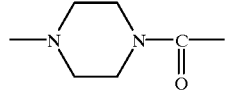

—NH—(CH$_2$)$_2$—NH—CO—, —NH—CH$_2$— or

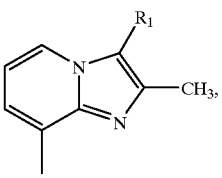

Q is a group selected from the group consisting of (Het 1)

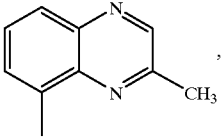

(Het 2)

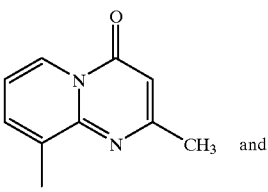

, (Het 3)

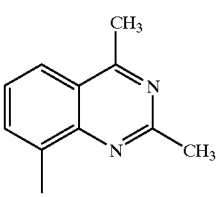

and (Het 4)

$R_1$ is a hydrogen atom, a halogen atom, or a $C_1$–$C_3$ alkyl group with a linear or branched hydrocarbon chain, $R_2$ is H, or its addition salts, said method comprising:

(1) reacting an alkali metal salt of a hydroxylated heterocyclic compound of the formula Q-O-Met in which:

Met is an alkali metal, and

Q is a heterocyclic group selected from the group consisting of Het 1, Het 2, Het 3 and Het 4:

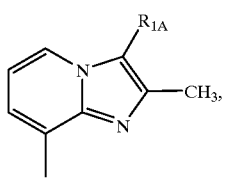
(Het 1)

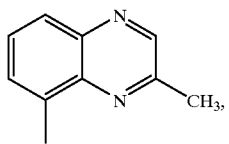
(Het 2)

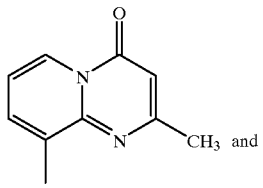
(Het 3)

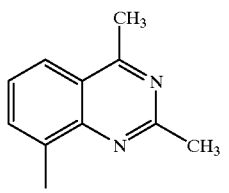
(Het 4)

$R_{1A}$ being a hydrogen atom or a $C_1$–$C_3$ alkyl group, with a compound of the formula II:

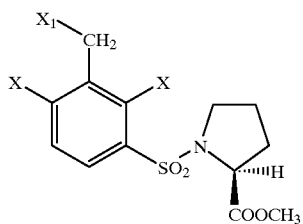
(II)

in which X is a halogen atom and $X_1$ is a halogen atom, in an anhydrous solvent, at a temperature of between 0 and 50° C., for 0.5 to 10 hours, to give a compound of the formula III:

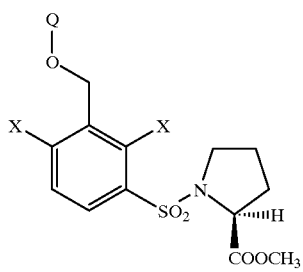
(III)

in which Q, X and $R_{1A}$ are as defined above;

(2) optionally, when Q in the compound of formula III is Het 1 in which $R_{1A}$ is a hydrogen atom, reacting said compound of the formula III with a halogenating agent in a solvent, at a temperature of between 0 and 50° C., for 0.5 to 20 hours, to give a compound of the formula III':

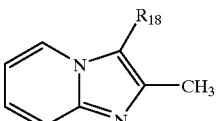
(III')

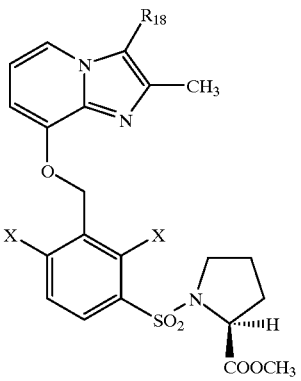

in which:

$R_{1B}$ is a halogen atom, (3) hydrolyzing the ester group of the compound of the formula III or III' at a temperature of from 20 to 60° C., for 1 to 5 hours, to give a compound of the formula IV:

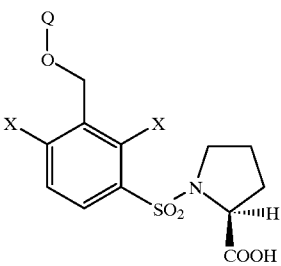
(IV)

in which Q and X are as defined above and $R_1$ is a hydrogen atom, a halogen atom or a $C_1$–$C_3$ alkyl group;

(4) reacting the compound of the formula IV with an amine of the formula

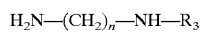
$H_2N—(CH_2)_n—NH—R_3$ or

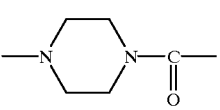

in which n is 2, 3 or 4 and $R_3$ is an amino-protecting group, in a solvent, at a temperature between 10–35° C., for 2 to 50 hours, to give a compound of the formula X:

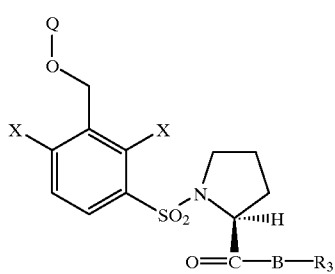

in which B is

—NH—(CH2)$_n$—NH— or

and Q, $R_1$, $R_3$ n and X are as defined above;

(5) deprotecting the amine group of the compound of the formula X so as to replace the group $R_3$ with a hydrogen atom, to give a compound of the formula XI:

(XI)

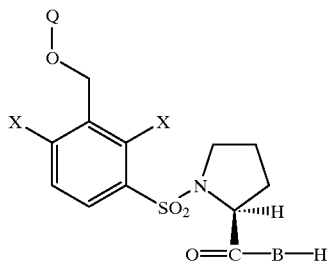

in which B, Q, $R_1$ and X are as defined above; and 6) reacting the compound of the formula XI with 4-(aminoiminomethyl)benzoic acid, in a solvent, at a temperature between 10–35° C., for 2 to 50 hours, to give a compound of the formula I:

(I)

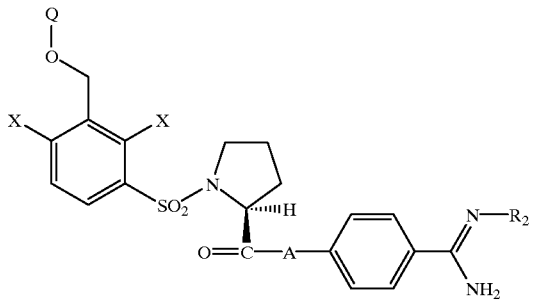

in which:

Q, $R_1$ and X are as defined above, $R_2$ is H, A is a group

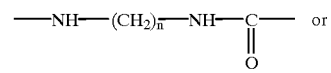 or

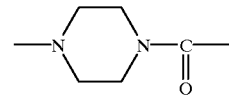

and n is as defined above.

8. A method for the preparation of a compound of the formula I:

(I)

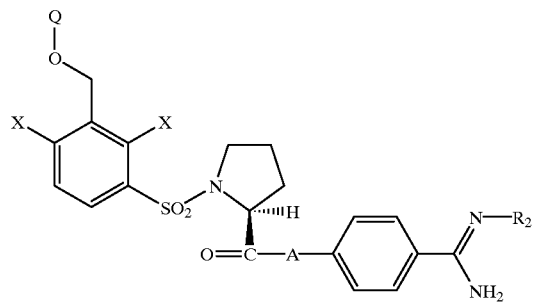

in which:

X is a halogen atom,

A is a divalent group

—NH—(CH$_2$)$_n$—NH—CO—, —NH—CH$_2$— or

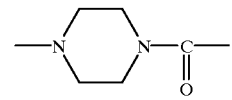

n is 2, 3 or 4,

Q is a group selected from the group consisting of (Het 1)

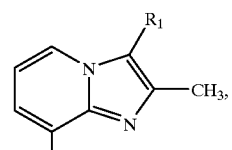

(Het 2)

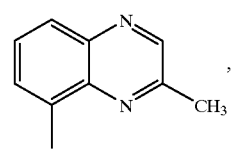

-continued

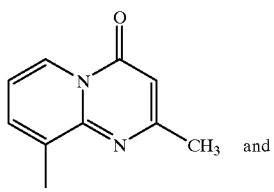
(Het 3)

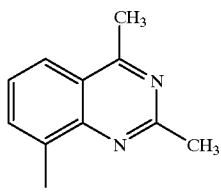
(Het 4)

R₁ is a hydrogen atom, a halogen atom, a $C_1$–$C_3$ alkyl group with a linear or branched hydrocarbon chain, or a $C_1$–$C_5$ 1-oxoalkyl group, and
R₂ is OH or H,
or its addition salts,
said method comprising:
(1) reacting an acid of the formula XII:

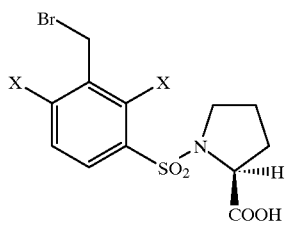
(XII)

in which X is a halogen atom, with a compound of the formula

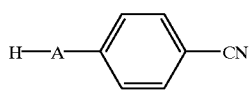

in which A is a group

—NH—(CH₂)ₙ—NH—CO—, —NH—CH₂— or

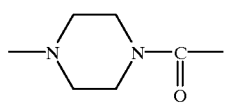

in which n is 2, 3 or 4,
in a solvent, at a temperature between 10–35° C., for 2 to 50 hours, to give a compound of the formula XIII:

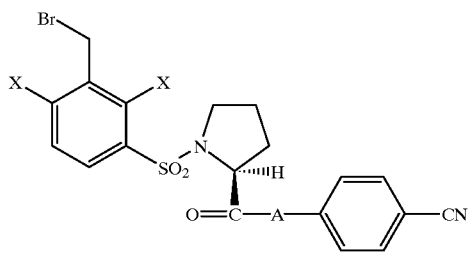
(XIII)

in which A and X are as defined above;

(2) reacting the compound of the formula XIII with a hydroxylated heterocyclic compound of the formula Q-OH, Q being selected from the group consisting of the structures:

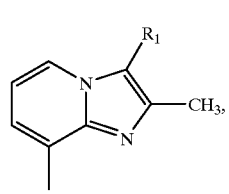
(Het 1)

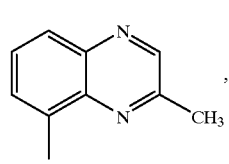
(Het 2)

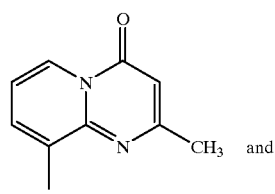
(Het 3)

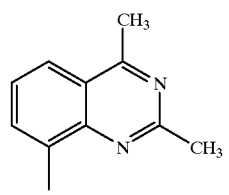
(Het 4)

in which R₁ is a hydrogen atom, a halogen atom, a $C_1$–$C_3$ alkyl group or a $C_1$–$C_5$ 1-oxoalkyl group, in an anhydrous solvent, at a temperature of between 0 and 50° C., for 0.5 to 10 hours, to give a compound of the formula XIV:

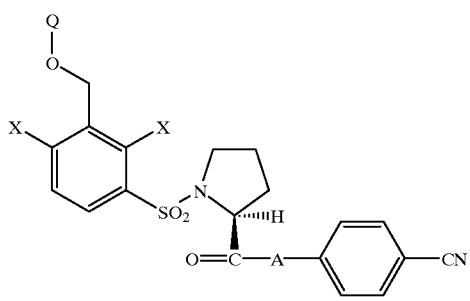

in which Q, R$_1$, X and A are as defined above;

(3) reacting the compound of the formula XIV with hydroxylamine in a solvent, at between 15–25° C., for 1 to 12 hours, to give a compound of the formula VIII:

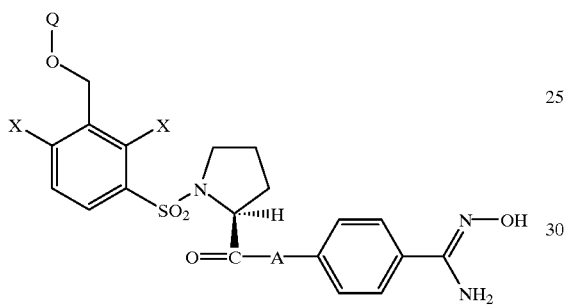

in which Q, R$_1$, X and A are as defined above, said compound VIII being a compound of the formula I wherein R$_2$ is OH;

(4) acetylating the compound of the formula VIII at a temperature between 10–35° C., for 1 to 8 hours, to give a compound of the formula IX:

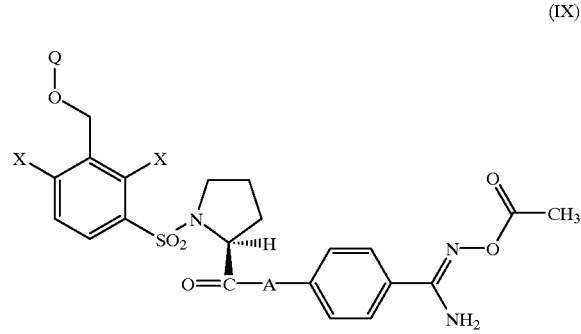

in which Q, R$_1$, X and A are as defined above; and (5) reducing the compound of the formula IX by catalytic hydrogenation, at a temperature between 10–35° C., under a hydrogen pressure of between $10^5$ and $10^6$ Pascals, to give a compound of the formula I in which Q, R$_1$, X and A are as defined above and R$_2$ is H.

* * * * *